(12) United States Patent
Tovar et al.

(10) Patent No.: US 8,871,903 B2
(45) Date of Patent: Oct. 28, 2014

(54) PALLADIUM CATALYZED REACTIONS EXECUTED ON SOLID-PHASE PEPTIDE SYNTHESIS SUPPORTS FOR THE PRODUCTION OF SELF-ASSEMBLING PEPTIDES EMBEDDED WITH COMPLEX ORGANIC ELECTRONIC SUBUNITS

(71) Applicant: The Johns Hopkins University, Baltimore, MD (US)

(72) Inventors: John D. Tovar, Baltimore, MD (US); Allix M. Sanders, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/657,219

(22) Filed: Oct. 22, 2012

(65) Prior Publication Data

US 2014/0114052 A1   Apr. 24, 2014

(51) Int. Cl.
| | | |
|---|---|---|
| *C07K 1/10* | (2006.01) | |
| *C07K 1/08* | (2006.01) | |
| *C07K 1/06* | (2006.01) | |
| *C07D 333/00* | (2006.01) | |
| *A61K 31/381* | (2006.01) | |

(52) U.S. Cl.
CPC ........................................ *C07K 1/10* (2013.01)
USPC ............ 530/328; 514/1.1; 514/183; 514/430; 514/438; 530/333; 530/334; 530/335

(58) Field of Classification Search
CPC .... C07D 331/00; C07D 333/00; A61K 38/00; A61K 38/02; A61K 31/38; A61K 31/381; A61K 31/33; C07K 1/00; C07K 1/10; C07K 1/06; C07K 1/061; C07K 1/08; C07K 1/063; C07K 1/084; C07K 2/00
See application file for complete search history.

(56) References Cited

U.S. PATENT DOCUMENTS

2012/0101022 A1*   4/2012   Tovar et al. .................... 514/1.1

OTHER PUBLICATIONS

Blackwell, H. E. et al., "Exploiting Site-Site Interactions on Solid Support to Generate Dimeric Molecules", Organic Letters, 2001, 3(8), pp. 1185-1188.
Bräse, S. et al., "Palladium-catalysed reactions in sold phase organic synthesis", Tetrahedron, 2003, 59(7), pp. 885-939.
Chen, L. et al., "Energy transfer in self-assembled dipeptide hydrogels", Chemical Communications, 2010, 46(24), pp. 4267-4269.
Conde-Frieboes, K. et al., "Synthesis of symmetrical dimeric N,N'-linked peptides on solid support by olefin metathesis", Tetrahedron Letters, 2000, 41(47), pp. 9153-9156.
Diegelmann, S. R. et al., "One-Dimensional Optoelectronic Nanostructures Derived from the Aqueous Self-Assembly of π-Conjugated Oligopeptides", Journal of American Chemical Society, 2008, 130(42), pp. 13840-13841.
Doan, N-D. et al., "Effectiveness of the Suzuki-Miyaura Cross-Coupling Reaction for Solid-Phase Peptide Modification", Journal of Combinatorial Chemistry, 2008, 10(1), pp. 44-51.
Guo, X. and Watson, M. D., "Conjugated Polymers from Naphthalene Bisimide", Organic Letters, 2008, 10(23), pp. 5333-5336.
Hou, J. et al., "Synthesis and Photovoltaic Properties of Two-Dimensional Conjugated Polythiophenes with Bi(thienylenevinylene) Side Chains", Journal of American Chemical Society, 2006, 128(14), pp. 4911-4916.
Kas, O. Y. et al., "Regulation of electronic behavior via confinement of PPV-based oligomers on peptide scaffolds" Journal of Materials Chemistry, 2008, 18(32), pp. 3847-3854.
Kilbinger, A. F. M. et al., "Chiral Aggregates of α,ωDisubstituted Sexithiophenes in Protic and Aqueous Media", Journal of American Chemical Society, 2000, 122(8), pp. 1820-1821.
Krieg, E. et al., "Supramolecular Gel Based on a Perylene Diimide Dye: Multiple Stimuli Responsiveness, Robustness, and Photofunction", Journal of American Chemical Society, 2009, 131(40), pp. 14365-14373.
Kumar, R. J. et al., "Hierarchical Self-Assembly of Semiconductor Functionalized Peptide α-Helices and Optoelectronic Properties", Journal of American Chemical Society, 2011, 133(22), pp. 8564-8573.
Le Quement, S. T. et al., "Solid-Phase Synthesis of Smac Peptidomimetics Incorporating Triazoloprolines and Biarylalanines", ACS Combinatorial Science, 2011, 13(6), pp. 667-675.
Liao, Y. et al., "Aliphatic Acetylenic Homocoupling Catalyzed by a Novel Combination of AgOTs-CuCl2-TMEDA and Its Application for the Solid-Phase Synthesis of Bis-benzo[b]furan-Linked 1,3-Diynes", Organic Letters, 2003, 5(6), pp. 909-912.
Liao, Y. et al., "Convergent Solid-Phase Synthesis of Symmetrical Benzo[b]furan's Dimerizer", Journal of Combinatorial Chemistry, 2003, 5(2), pp. 79-81.
Luo, F. et al., "Palladium-catalyzed reduction of alkynes employing HSiEt3: stereoselective synthesis of trans- and cis-alkenes", Tetrahedron, 2010, 66(6), pp. 1399-1403.
Olenyuk, B. et al., "Parallel Synthesis of H-pin Polyamides by Alkene Metathesis on Solid Phase", Journal of American Chemical Society, 2003, 125(16), pp. 4741-4751.
Schillinger, E. et al., "Oligothiophene Versus β-Sheet Peptide: Synthesis and Self-Assembly of an Organic Semiconductor-Peptide Hybrid", Advanced Materials, 2009, 21(16), pp. 1562-1567.
Shao, H. and Parquette, J. R., "A π-conjugated hydrogel based on an Fmoc-dipeptide naphthalene diimide semiconductor", Chemical Communications, 2010, (46(24), pp. 4285-4287.
Shaytan, A. K. et al., "Self-Assembling Nanofibers from Thiophene-Peptide Diblock Oligomers: A Combined Experimental and Computer Stimulations Study", ACS Nano, 2011, 5(9), pp. 6894-6909.
Stone, D. A. et al., "Self-assembling quinquethiophene-oligopeptide hydrogelators", Soft Matter, 2009, 5(10), pp. 1990-1993.
Sun, Y. et al., Fine-Tuned Nanostructures Assembled from L-Lysine-Functionalized Perylene Bisimides, Langmuir, 2011, 27(18), pp. 11364-11371.
Testero, S. A. and Mata, E. G., "Prospect of Metal-Catalyzed C-C Forming Cross-Coupling Reactions in Modern Solid-Phase Organic Synthesis", Journal of Combinatorial Chemistry, 2008, 10(4), pp. 487-497.

(Continued)

Primary Examiner — Karlheinz R Skowronek
Assistant Examiner — Catherine Mader
(74) Attorney, Agent, or Firm — Ward and Smith, P.A.

(57) ABSTRACT

Methods to synthesize self-assembling peptides embedded with complex organic electronic subunits are provided.

7 Claims, 10 Drawing Sheets

(56) References Cited

OTHER PUBLICATIONS

Tian, L. et al., "Development of a robust supramolecular method to prepare well-defined nanofibrils from conjugated molecules", Chemical Science, 2012, 3(5), pp. 1512-1521.

Vadehra, G. S. et al., "On-resin dimerization incorporates a diverse array of π-conjugated functionality within aqueous self-assembling peptide backbones", Chemical Communications, 2010, 46(22), pp. 3947-3949.

Wall, B. D. et al., "Aligned Macroscopic Domains of Optoelectronic Nanostructures Prepared via Shear-Flow Assembly of Peptide Hydrogels", Advanced Materials, 2011, 23(43), pp. 5009-5014.

* cited by examiner

PALLADIUM CATALYZED REACTIONS EXECUTED ON SOLID-PHASE PEPTIDE SYNTHESIS SUPPORTS FOR THE PRODUCTION OF SELF-ASSEMBLING PEPTIDES EMBEDDED WITH COMPLEX ORGANIC ELECTRONIC SUBUNITS

FEDERALLY SPONSORED RESEARCH OR DEVELOPMENT

This invention was made in part with United States Government support under DE-SC0004857 awarded by the Department of Energy (DOE). The U.S. Government has certain rights in the invention.

BACKGROUND

Peptide-based π-electron scaffolds offer a unique ability to encourage exciton coupling among π-conjugated subunits in aqueous environments (Ashkenasy et al., 2006; Krieg et al., 2009; Chen et al., 2010; Shao et al., 2010; Sun et al., 2011; Tian et al., 2012; Kas et al., 2008; Kumar et al., 2011; Diegelmann et al., 2008; Schillinger et al., 2009; Stone et al., 2009; Shaytan et al., 2011; Wall et al., 2011; Mba et al., 2011; Vadehra et al., 2010). These scaffolds promote delocalized electronic states among the component conjugated oligomers and, due to their peptidic nature, offer an enticing segue into biological investigations. Current state of the art consists of molecular structures, such as synthetic polypeptides or genetically modified α-helical proteins, which position π-conjugated oligomers with defined spatial orientations, thereby leading to collective electronic delocalization among otherwise isolated electronic units (Kas et al., 2008; Kumar et al., 2011). Likewise, π-electron peptidic materials can be directed to aggregate into nanostructured materials with tube or tape-like morphologies (Diegelmann et al., 2008; Schillinger et al., 2009; Stone et al., 2009; Shaytan et al., 2011; Wall et al., 2011; Mba et al., 2011; Vadehra et al., 2010). Many of the common synthetic approaches to install the requisite π-electron units involve solution-phase reactions between the π-conjugated segments and the peptide fragments, using reactive functional groups, such as amines or carboxylic acids (for amide bond formation) or alkynes (for Huisgen-type cycloadditions). These examples, however, require the upfront chemical synthesis of the conjugated oligomer of interest appended with the necessary reactive groups to allow for ligation onto or within the peptide framework, thus posing challenges for mutual peptide/chromophore solubility and for final construct purification.

An alternative synthetic strategy was recently reported that keeps the peptides bound to solid supports during the installation of the π-electron segments via site-site double amidation between immobilized peptides and π-conjugated diacids (Vadehra et al., 2010). This approach still requires the synthesis of the diacid components, and the solubilities of the critical π-electron segments become problematic as the conjugated oligomer is made longer.

SUMMARY

In some aspects, the presently disclosed subject matter provides a method for preparing one or more peptide-[($Ar^1$—$Ar^2$—$Ar^1$)]-peptide structures, the method comprising: (a) providing one or more peptides immobilized on a solid support, wherein the one or more peptides have a deprotected or free amine group; (b) contacting the one or more immobilized peptides with a portion of a i-conjugated subunit comprising a first arene ($Ar^1$) and differentially substituted with a halide and a carboxylic acid group to promote N-acylation of the amine termini of the one or more peptides; (c) contacting the one or more immobilized peptides of step (b) with a second arene ($Ar^2$) disubstituted with mutually reactive functionality for transmetallation in the presence of a palladium catalyst to promote site-site cross coupling between the disubstituted second arene and the two N-acylated amine termini of the one or more peptides formed in step (b); and (d) cleaving the product formed in step (c) to form one or more peptide-[($Ar^1$—$Ar^2$—$Ar^1$)]-peptide structures. In further aspects, the presently disclosed subject matter provides a peptide-[($Ar^1$—$Ar^2$—$Ar^1$)]-peptide structure prepared by the method disclosed immediately hereinabove. In particular aspects, the one or more peptide-[($Ar^1$—$Ar^2$—$Ar^1$)]-peptide structures have a property of self assembly into a defined nanostructure when combined with identical or different one or more peptide-[($Ar^1$—$Ar^2$—$Ar^1$)]-peptide structures under aqueous or physiological conditions.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
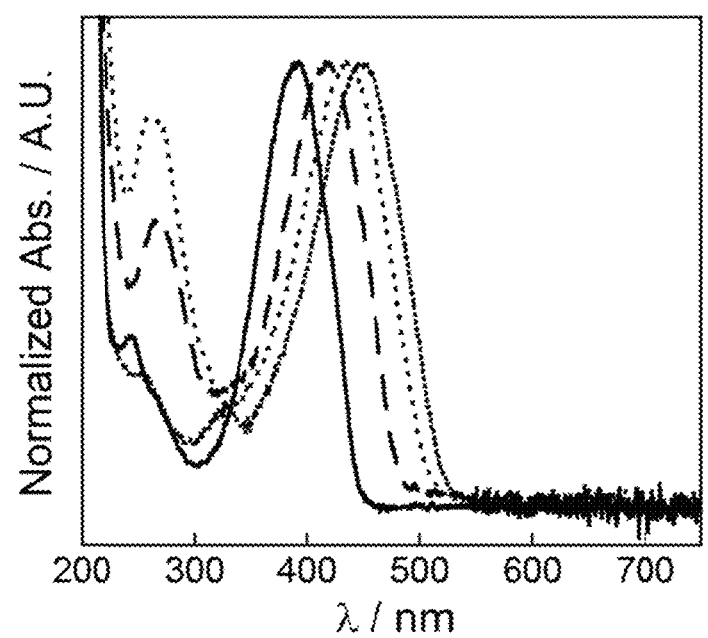
Figure 3:
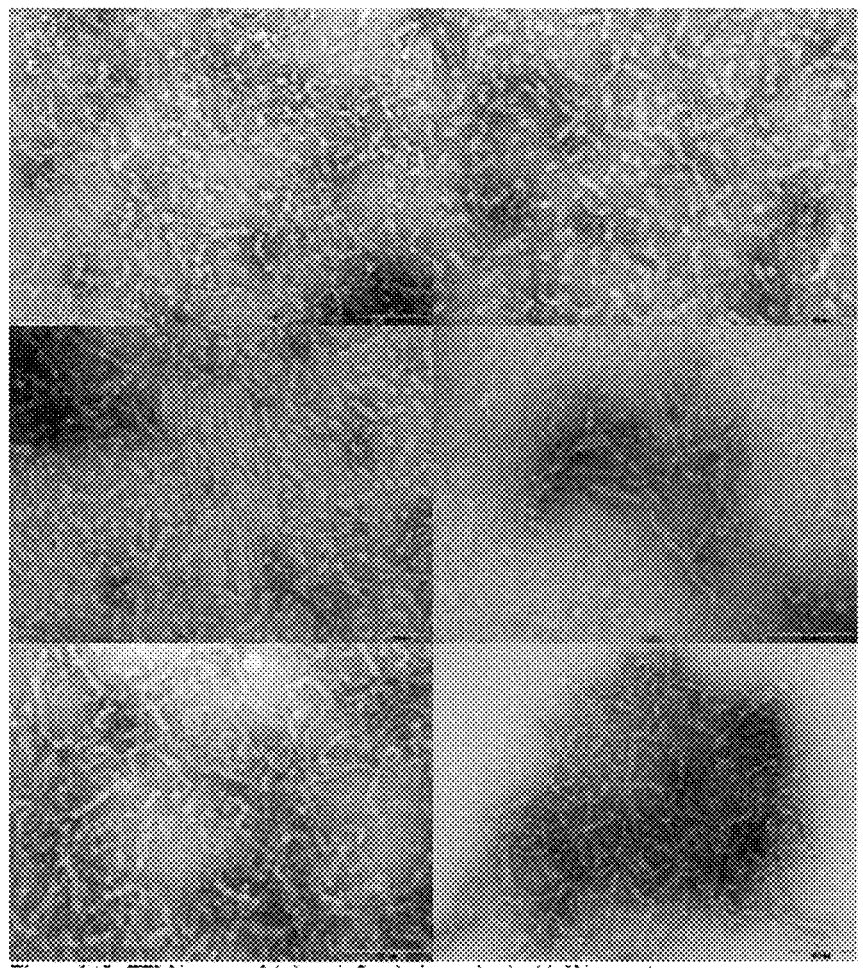
Figure 4:
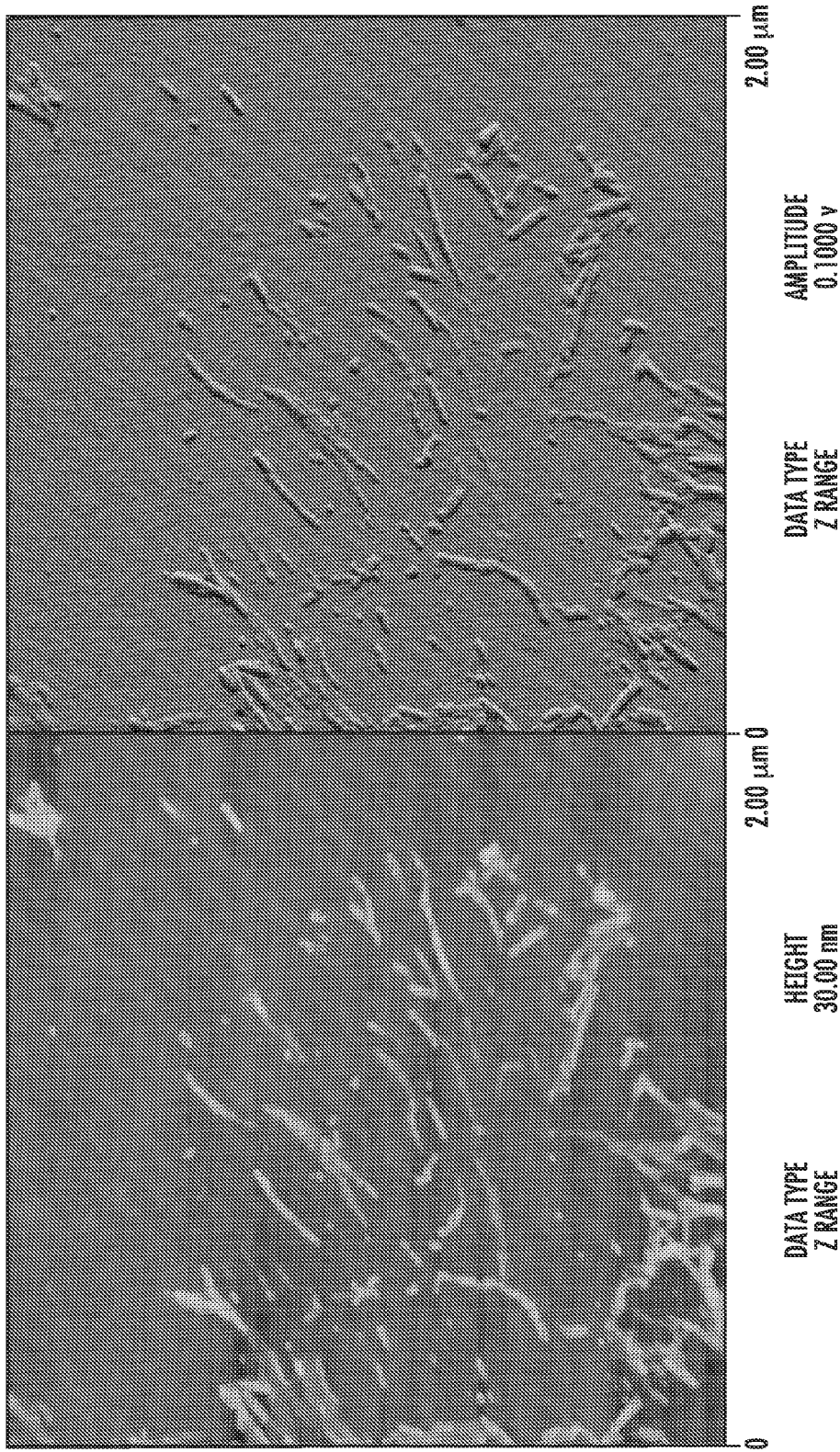

Having thus described the presently disclosed subject matter in general terms, reference will now be made to the accompanying Figures, which are not necessarily drawn to scale, and wherein:

FIG. 1 is normalized UV-vis spectra of unassembled 1 (_____) 2 (_ _ _ _), 3 (••••), and 4 (•••••) in pH 8 water;

FIGS. 2a-2f show: (a) an illustration of a β-sheet network and (b) space-filling model illustrating nanostructures formed from assembly of a generic oligothiophene peptide; UV-vis and photoluminescence (c) and CD spectra (d) of 4 in acidic (assembled, solid line) and basic (unassembled, dashed line) water; TEM images of nanostructures of 3 showing an extensive network (e) and solitary structures (f, diameter: 6-8 nm, molecule in most extended conformation: 4.9 nm.);

FIG. 3. shows TEM images of 4. (1 mg/mL solution stained with 2% uranyl acetate. Nanostructure diameter: 5-8 nm, molecule in most extended conformation: 5.2 nm.);

FIG. 4. shows a AFM height scan (left) and amplitude scan (right) of 3. (0.1 mg/mL solution dropcasted on $SiO_2$. Nanostructures generally displayed an average height between 3 and 6 nm, with a few displaying heights of approximately 2 nm.)

Figure 5:
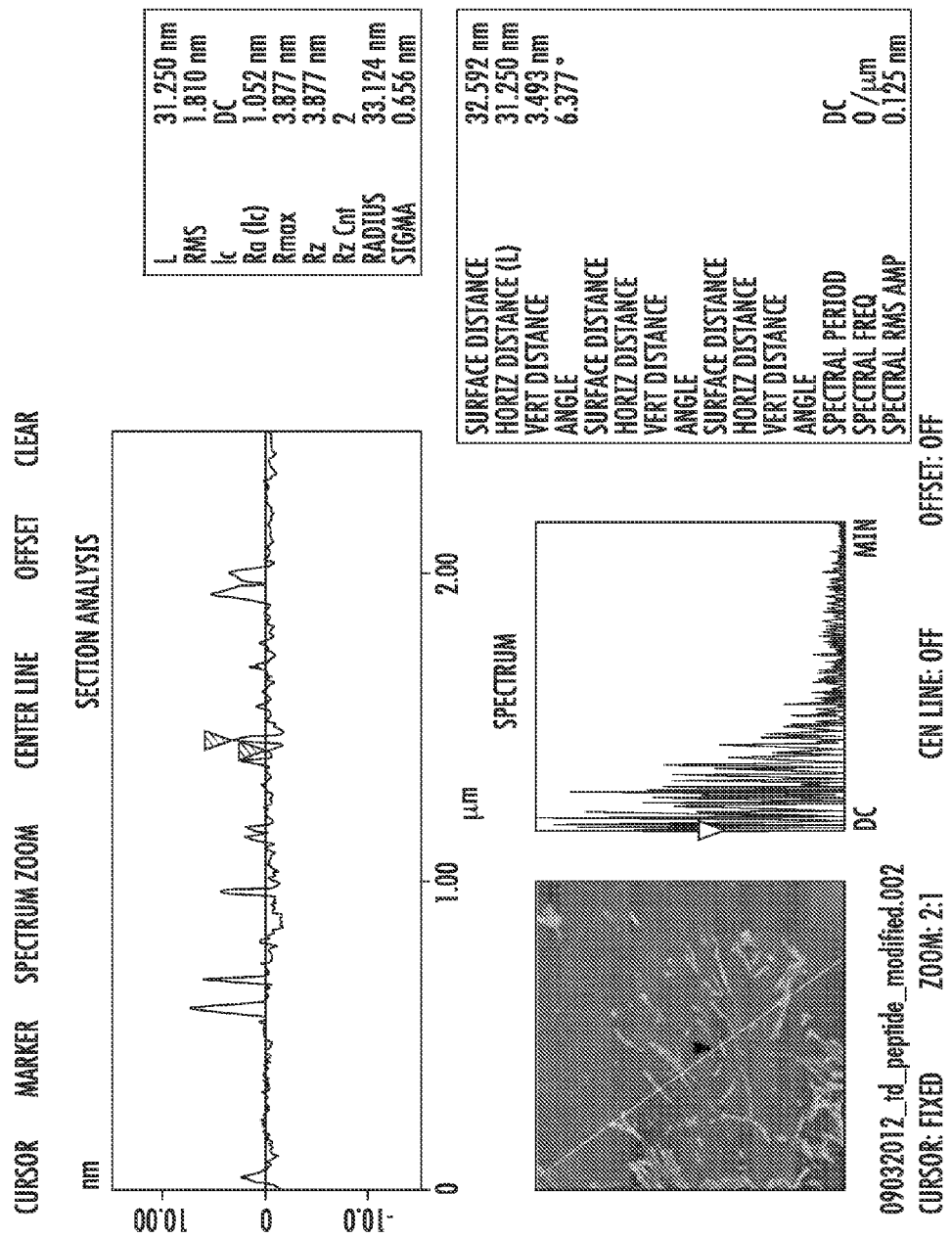
Figure 6:
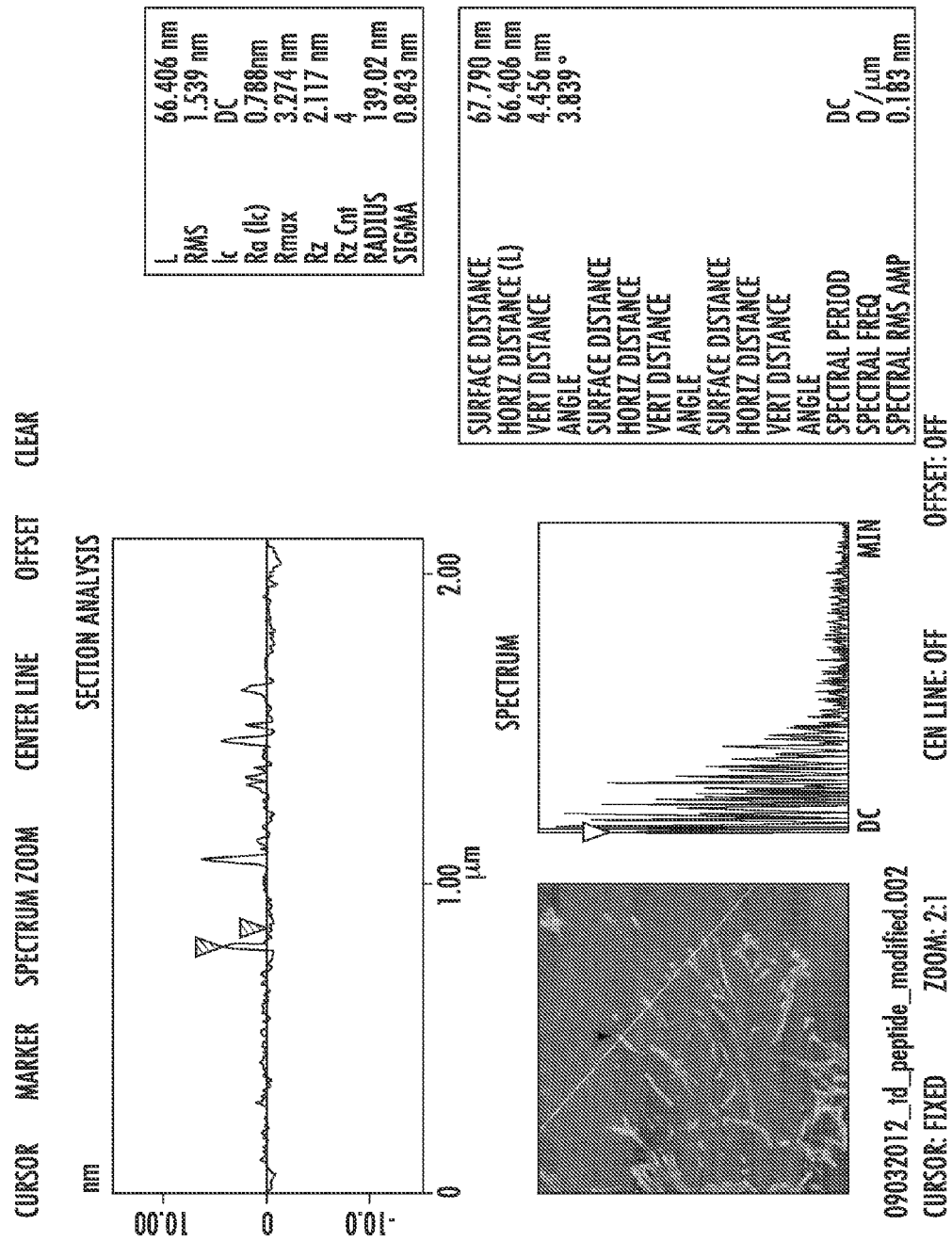
Figure 7:
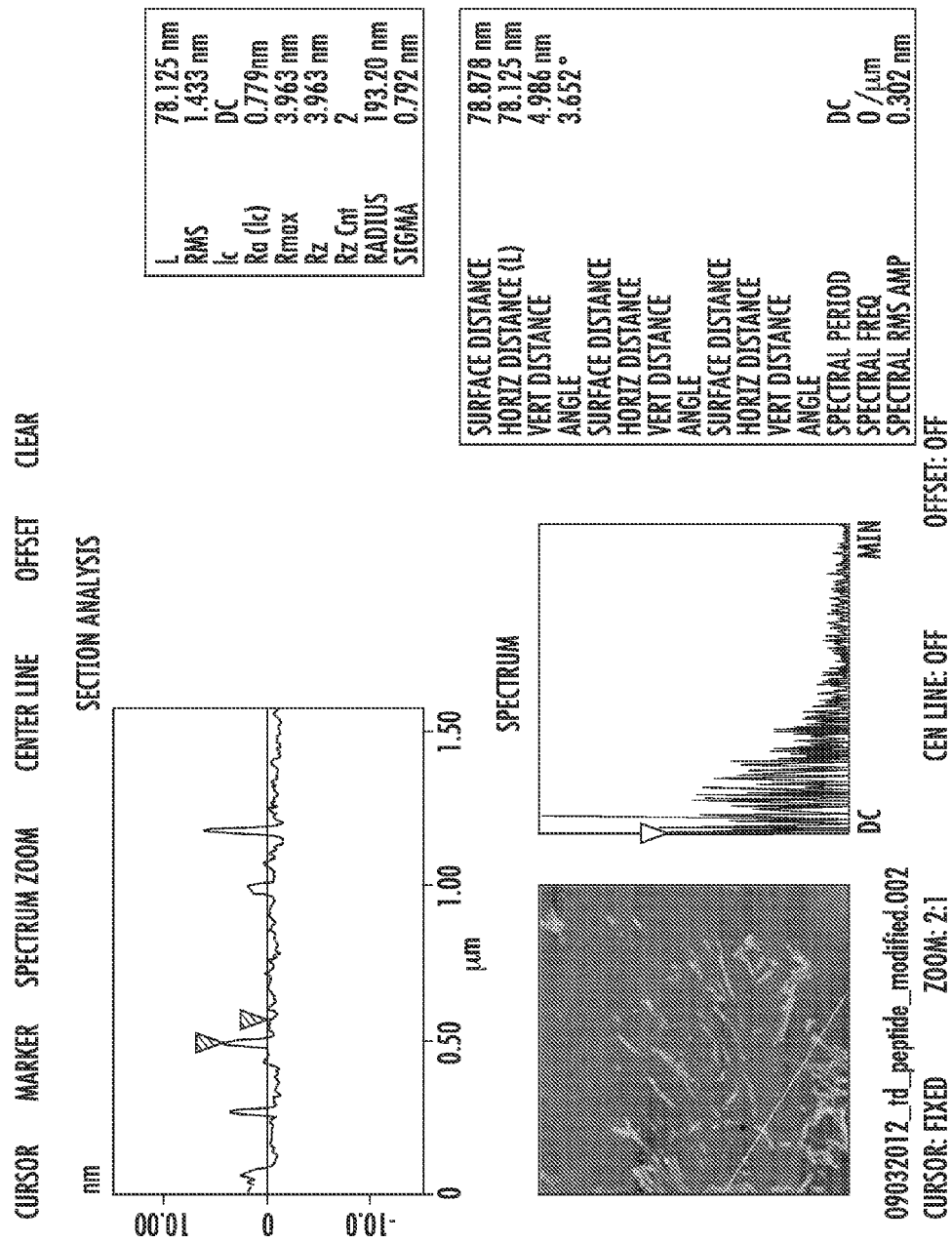
Figure 8:
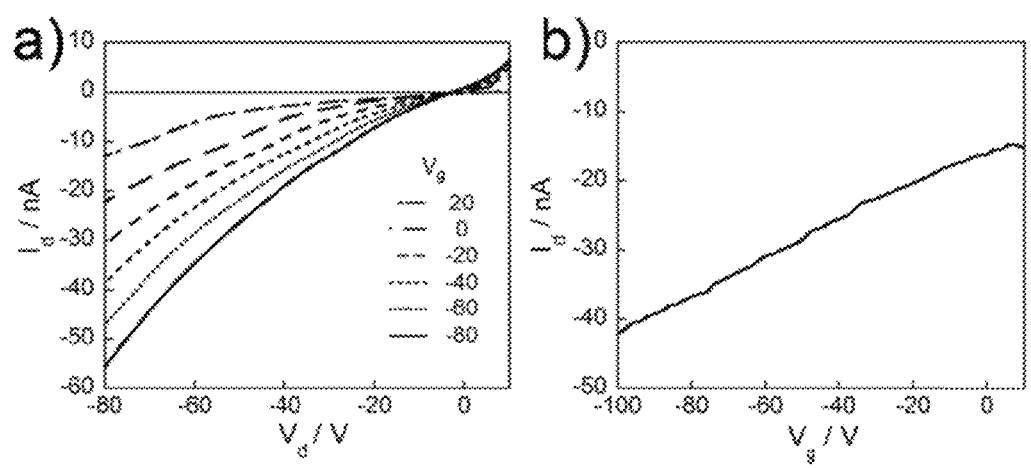
Figure 9:
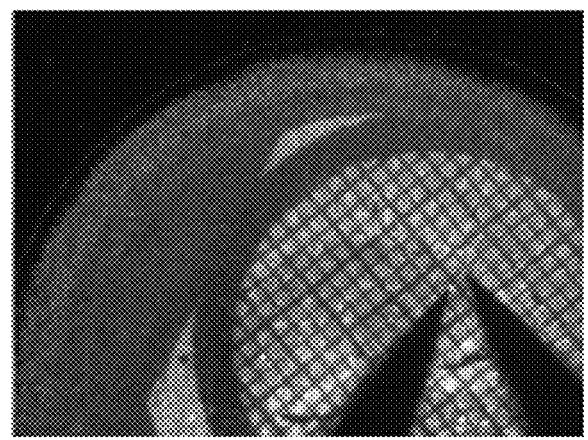
Figure 10:
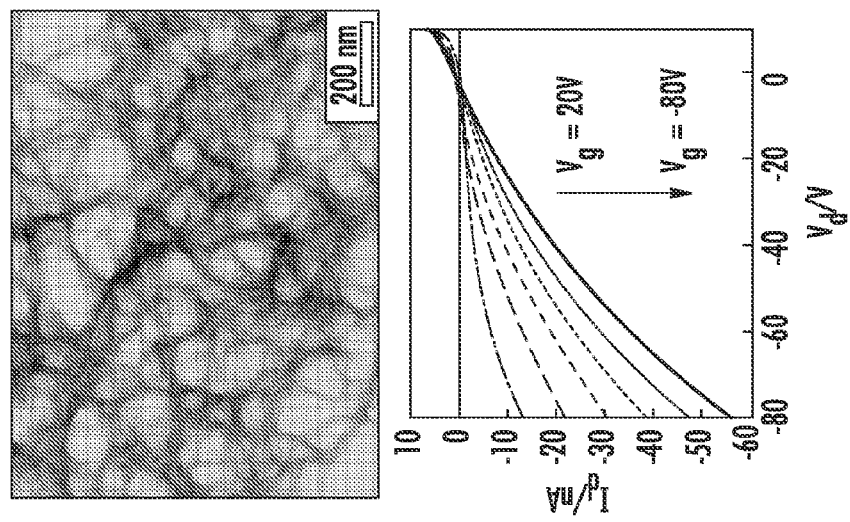
Figure 10:
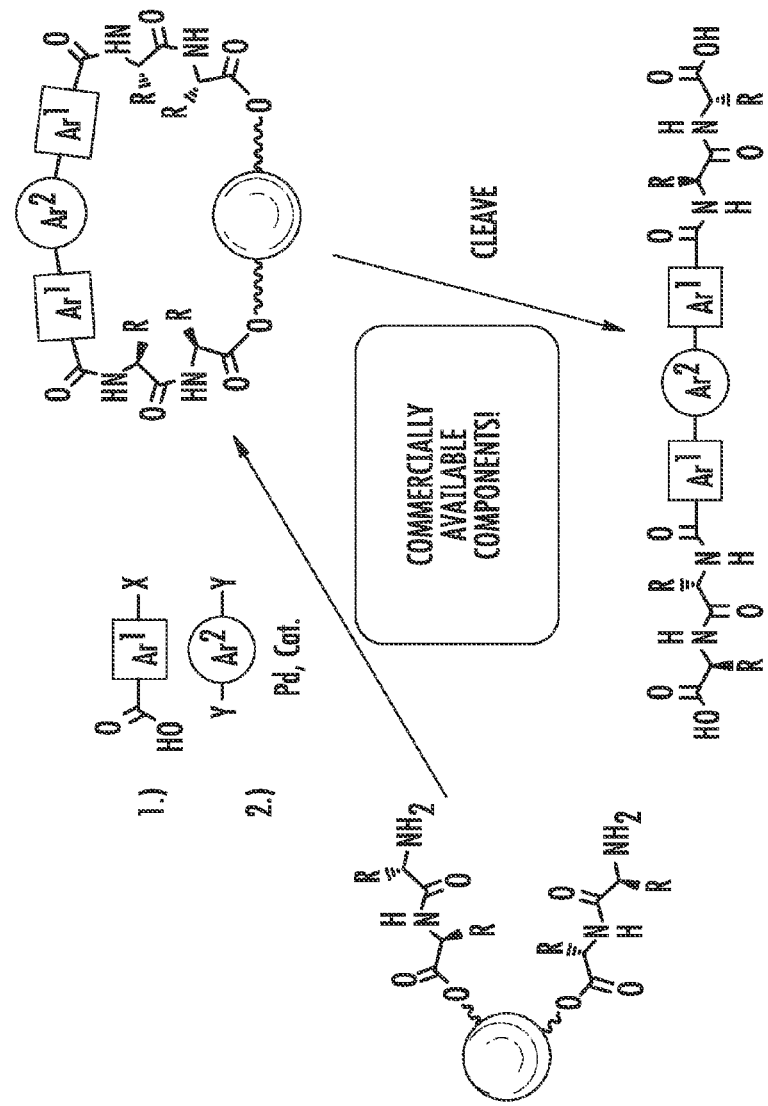

FIG. 5. shows a height profile of 3. (0.1 mg/mL solution dropcasted on $SiO_2$. Nanostructure height (indicated with arrows): 3.493 nm, molecule in most extended conformation: 4.9 nm.);

FIG. 6 shows a height profile of 3. (0.1 mg/mL solution dropcasted on $SiO_2$. Nanostructure height (indicated with arrows): 4.456 nm, molecule in most extended conformation: 4.9 nm.);

FIG. 7 shows a height profile of 3. (0.1 mg/mL solution dropcasted on $SiO_2$. Nanostructure height (indicated with arrows): 4.986 nm, molecule in most extended conformation: 4.9 nm.);

FIGS. 8a and 8b are current-Voltage response plots of a field-effect transistor of 4 (a) at gate voltages of 20V to −80V, with varied applied drain voltage and (b) at an applied drain voltage of −80V, with varied applied gate voltage;

FIG. 9 shows a light microscope image of dropcast film of 4 incorporated into FET, showing deposited electrodes (via TEM grid shadow mask) and contact positioning; and FIG. 10 shows a schematic of the solid-phase palladium catalyzed cross-coupling procedure, TEM images of nanostructures of 3 showing an extensive network (as in FIG. 2e), and current-Voltage response plots of a field-effect transistor of 4 (as in FIG. 8a).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

I. PALLADIUM CATALYZED REACTIONS EXECUTED ON SOLID-PHASE PEPTIDE SYNTHESIS SUPPORTS FOR THE PRODUCTION OF SELF-ASSEMBLING PEPTIDES EMBEDDED WITH COMPLEX ORGANIC ELECTRONIC SUBUNITS

Synthetic strategies that keep the peptides bound to solid supports during the installation of the π-electron segments via site-site double amidation between immobilized peptides and π-conjugated diacids require the synthesis of the diacid components, and the solubilities of the critical π-electron segments become problematic as the conjugated oligomer is made longer (Vadehra et al., 2010). To circumvent these problems, the presently disclosed subject matter utilizes the power of Pd-mediated (palladium-mediated) cross-coupling as a tool to provide diverse π-conjugated systems that incorporate several different aryl-aryl linkages embedded within self-assembling peptide architectures through the union of small, soluble components, many of which are readily available commercially. This remarkably facile approach in principle eliminates the need for lengthy solution-phase purification of synthesis intermediates.

The presently disclosed methods also evade problematic solubility issues to access conjugated units up to sexithiophene, which is thought to be the longest peptide-embedded oligothiophene to be rendered water soluble yet still able to self-assemble into semiconductive 1-D nanostructures. Although transition metal-mediated chemistries have been utilized on solid supports (Deshpande, 1994; Malenfant, 1998; Conde-Frieboes et al., 2000; Blackwell et al., 2001; Bräse et al., 2003; Liao et al., 2003; Liao et al., 2003; Doan et al., 2008; Testero et al., 2008; Le Quement et al., 2011), the presently disclosed subject matter provides a unique example of solid-phase palladium-catalyzed cross-coupling dimerizations. This approach allows for the facile preparation of aqueous self-assembling systems that encourage the intermolecular electronic delocalization among tunable π-electron segments within well-defined 1-D nanostructures.

Accordingly, described herein is a strategy to embed complex π-conjugated units within peptidic architectures through the use of solid-phase palladium catalyzed reactions. Following standard solid-phase peptide synthesis, various types of palladium catalyzed cross-couplings are utilized to perform dimerizations on the solid-phase resulting in complex, electronically active subunits. This synthesis strategy allows for the construction of complex electronic function within peptide-based biomaterials, while requiring minimal (or no) synthetic and purification steps. Further, these synthetic manipulations are completed in conjunction with solid-phase peptide synthesis to provide π-conjugated peptides of higher complexity, and potential electronic functionality, than have previously been accessible. The presently disclosed methods can be applied to create a variety of different electronically active subunits by providing a simple means to tune the electronic characteristics of the materials.

Representative embodiments of the presently disclosed synthetic strategy are illustrated in Scheme 1.

Scheme 1. Solid-phase palladium catalyzed cross-couping procedure.

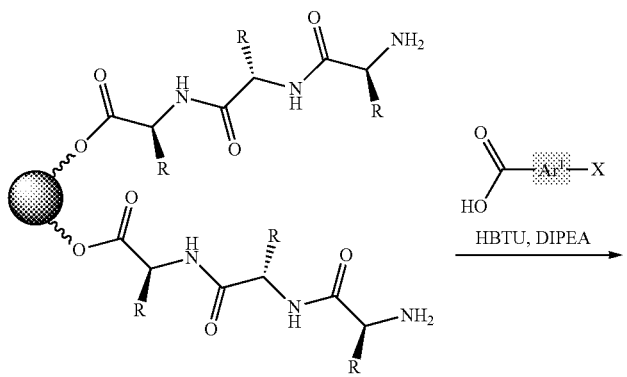

HBTU, DIPEA

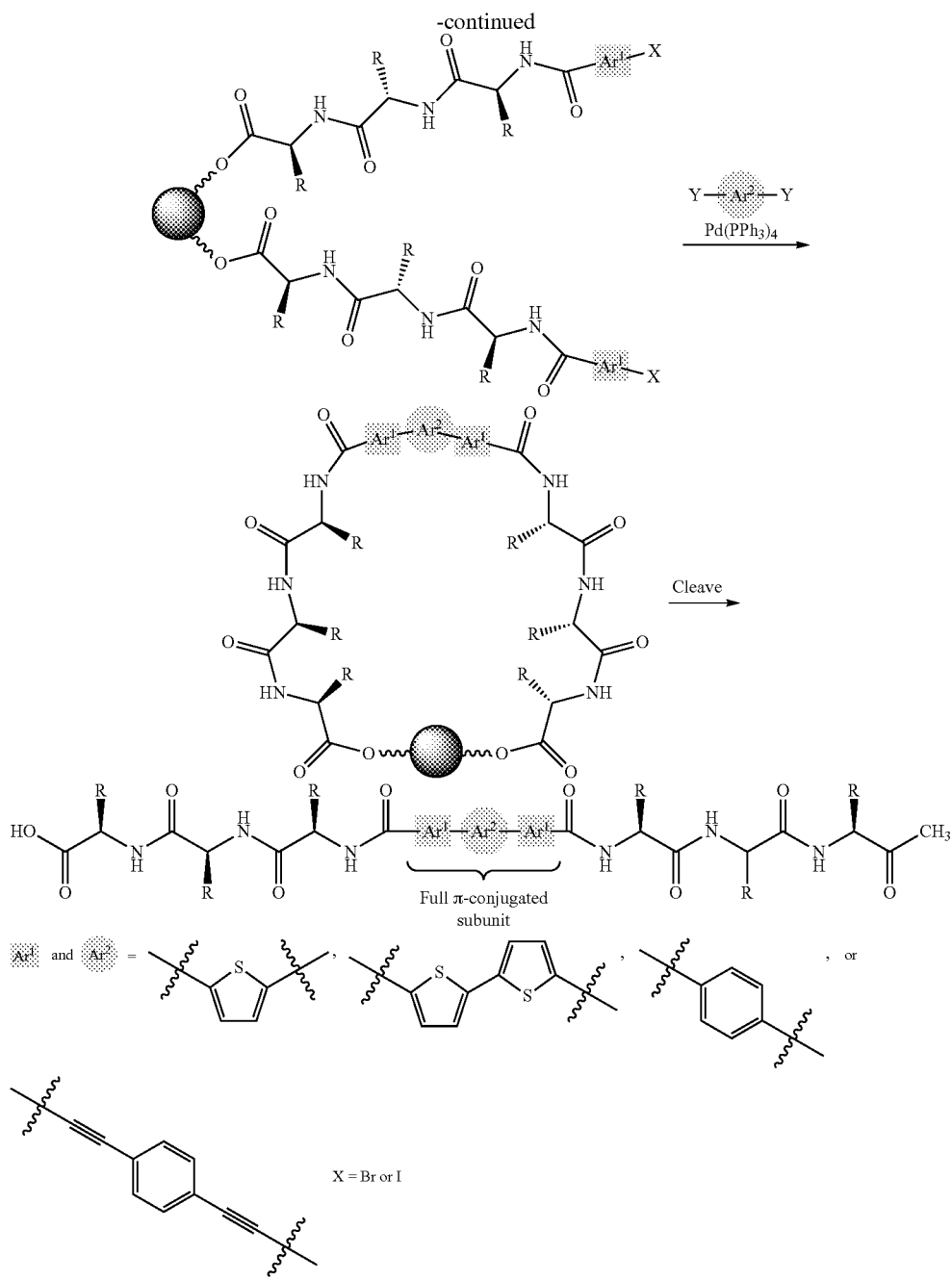

In some embodiments, a small oligopeptide, immobilized on a resin bead, is synthesized via standard Fmoc solid phase peptide synthesis (SPPS). A portion of the π-conjugated subunit ($Ar^1$=thiophene, bithiophene, phenyl, or diethynylphenyl), differentially substituted with a halide (Br or I) and a carboxylic acid group (e.g. 4-iodobenzoic acid), is added to the resin under standard amino acid coupling conditions. N-acylation of the amine termini of the peptide fragments with the in situ activated carboxylic acid moiety on $Ar^1$ immobilizes the aryl halide on the solid phase. A second arene ($Ar^2$), disubstituted with mutually reactive functionality for transmetallation under palladium catalysis, is introduced to the resin so that site-site cross coupling can occur. Using either a distannylated $Ar^2$ (Y=$SnBu_3$) under Stille conditions, a diboronic acid (Y=$B(OH)_2$) under Suzuki conditions, or diethynyl benzene (Y=C≡CH) under Sonogashira conditions, with $Pd(PPh_3)_4$ as the catalyst, coupling between the disubstituted $Ar^2$ segment and two aryl halides takes place. Upon cleavage and isolation, peptides embedded with $Ar^1$—$Ar^2$—$Ar^1$ π-conjugated oligomeric subunits are obtained.

Several approaches exist to create nanomaterials via the assembly of π-electron units in organic solvents, but general design strategies to do so in aqueous (and physiologically relevant) environments are not as well established. The presently disclosed self-assembly methods do not require an organic solvent. Said another way, the presently disclosed materials can undergo self assembly in the absence of, or essentially in the absence of, an organic solvent.

The method has proven versatile in the straightforward synthesis of a wide range of π-conjugated peptides. This diverse library of bioelectronic nanomaterials includes a complex sexithiophene-containing peptide whose nanostructures display gate-induced conductivity within field effect transistors. The presently disclosed subject matter provides peptide-based supramolecular semiconductor nanomaterials via Pd-catalyzed solid-phase dimerizations.

More particularly, in some embodiment, the presently disclosed subject matter provides a method for preparing one or more peptide-[(Ar$^1$—Ar$^2$—Ar$^1$)]-peptide structures, the method comprising: (a) providing one or more peptides immobilized on a solid support, wherein the one or more peptides have a deprotected or free amine group; (b) contacting the one or more immobilized peptides with a portion of a π-conjugated subunit comprising a first arene (Ar$^1$) and differentially substituted with a halide and a carboxylic acid group to promote N-acylation of the amine termini of the one or more peptides; (c) contacting the one or more immobilized peptides of step (b) with a second arene (Ar$^2$) disubstituted with mutually reactive functionality for transmetallation in the presence of a palladium catalyst to promote site-site cross coupling between the disubstituted second arene and the two N-acylated amine termini of the one or more peptides formed in step (b); and (d) cleaving the product formed in step (c) to form one or more peptide-[(Ar$^1$—Ar$^2$—Ar$^1$)]-peptide structures.

In particular embodiments, the first arene and the second arene can be the same or different and are each independently selected from the group consisting of thiophenyl, bithiophenyl, phenyl, and 1,4-diethynylphenyl. In more particular embodiments, the halide is selected from the group consisting of bromine and iodine. In certain embodiments, the palladium catalyst is Pd(PPh$_3$)$_4$.

In some embodiments, the one or more peptide-[(Ar$^1$—Ar$^2$—Ar$^1$)]-peptide structures are water soluble. In particular embodiments, the one or more peptide-[(Ar$^1$—Ar$^2$—Ar$^1$)]-peptide structures are selected from the group consisting of compounds 1-8 provided herein below in Table 1.

In further embodiments, the presently disclosed subject matter provides a peptide-[(Ar$^1$—Ar$^2$—Ar$^1$)]-peptide structure prepared by the method disclosed immediately hereinabove. In particular embodiments, the one or more peptide-[(Ar$^1$—Ar$^2$—Ar$^1$)]-peptide structures have a property of self assembly into a defined nanostructure when combined with identical or different one or more peptide-[(Ar$^1$—Ar$^2$—Ar$^1$)]-peptide structure under aqueous or physiological conditions.

In other embodiments, the presently disclosed subject matter provides a defined nanostructure comprising one or more peptide-[(Ar$^1$—Ar$^2$—Ar$^1$)]-peptide structures prepared by the method disclosed immediately hereinabove. In some embodiments, the defined nanostructure has at least one sub-10 nm dimension. In particular embodiments, the defined nanostructure comprises π-stacked electronic conduits comprising one or more peptide-[(Ar$^1$—Ar$^2$—Ar$^1$)]-peptide structures. In more particular embodiments, the defined nanostructure has a property selected from the group consisting of an electronic property and an optoelectronic property.

The presently disclosed subject matter can be used in a wide variety of applications. In some embodiments, the presently disclosed structures can be used as nanomaterials for electronic applications that do not need to be fabricated with lithography. In other embodiments, the peptide-[(Ar$^1$—Ar$^2$—Ar$^1$)]-peptide structures can be used as new materials for biomedicine with externally tunable properties that might be able to influence or detect cell-nanomaterial interactions and subsequent physiological impacts. Examples of externally tunable properties include, but are not limited to, variable surface charging, wettability, surface packing based upon charge injection-redox mediated by an external electrical source or by incident light, and the like. In further embodiments, the presently disclosed structures can be used as materials for biosensing or as imaging agents where interactions with biological matter perturb optoelectronic properties in a measurable manner.

II. DEFINITIONS

As used herein, the term "organic electronic unit" is used interchangeably with the terms "π-conjugated segment," "π-conjugated oligomer," and "π-conjugated unit" and is intended to mean a molecule, a portion of a molecule or a chemical moiety comprising one or more conjugated linkages of arenes, heteroarenes, and other unsaturated groups, such alkenes, alkynes, and the like, having delocalized i-electron properties as will be understood by those of skill in the art.

As used herein, the term "arene" includes monocyclic and polycyclic aromatic hydrocarbons. Representative arenes include benzene and substituted benzenes, biphenylene, and substituted biphenylenes. Representative polycyclic aromatic hydrocarbons include naphthalene, acenaphthylene, acenaphthene, fluorene, phenanthrene, anthracene, fluoranthene, pyrene, perylene, benz[a]anthracene, chrysene, benzo[b]fluoranthene, benzo[k]fluoranthene, benzo[a]pyrene, dibenz[a,h]anthracene, benzo[g,h,i]perylene, and indeno[1,2,3-cd]pyrene.

As used herein the term "heteroarene" includes heterocyclic compounds derived from arenes by replacement of one or more methine (—C═) and/or vinylene (—CH═CH—) groups by trivalent or divalent heteroatoms, e.g., oxygen, nitrogen, and sulfur, respectively, in such a way as to maintain the π-electron system characteristic of aromatic systems. Thiophene is an example of a heteroarene.

Alkenes include acyclic branched or unbranched hydrocarbons having at least one carbon-carbon double bond and the general formula $C_nH_{2n}$.Alkynes include acyclic branched or unbranched hydrocarbons having a carbon-carbon triple bond and the general formula $C_nH_{2n-2}$, RC≡CR. One of ordinary skill in the art would recognize that hydrocarbon radicals can be derived from the hydrocarbon moieties defined hereinabove by removal of one or more hydrogen atoms such that all valencies are satisfied when the radical is included in one or more of the presently disclosed compounds and materials.

As used herein, an "oligomer" includes a few monomer units, for example, in contrast to a polymer that potentially can comprise an unlimited number of monomers. Dimers, trimers, and tetramers are non-limiting examples of oligomers.

The organic electronic units can be varied, for example, to include fluorescent materials, electroactive materials, and/or materials that might have environmentally sensitive optoelectronic properties. Such organic electronic units include, for example, the α-oligothiophenes (bithiophene, terthiophene, quaterthiophene, and the like) used for p-channel (hole-transporting) organic semiconductors, oligophenylenes, the rylene diimides (naphthalene and perylene diimides, and the like) used for dyestuffs and for n-channel (electron-transporting) organic semiconductors, and the oligo(p-phenylene vinylenes) used as intense fluorophores for light emission and as dyes for photovoltaics. Other suitable examples of organic electronic units will be evident to those of skill in the art.

As used herein, the term "peptide segment", "oligopeptide", or "peptide" is intended to mean in some embodiments a peptide of 2 to 100 amino acid residues, including any integer from 2 to 100, and in some embodiments, 2 to 15 amino acid residues, including 2, 3, 4, 5, 6, 7, 8, 9, 10, 11, 12, 13, 14, and 15 amino acid residues, which are obtainable by standard peptide synthesis protocols known in the art. In other embodiments, a "peptide" can mean a protein comprising more than 100 amino acids, such as from about 100 to about 150 amino acids, from about 150 to about 200 amino acids, and the like.

As used herein, an "amino acid residue" is a residue of a naturally occurring amino acid or a variant thereof, including but not limited to alanine (A), arginine (R), asparagine (N), aspartate (D), cysteine (C), glutamate (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), valine (V), 5-hydroxylysine, 4-hydroxyproline, thyroxine, 3-methylhistidine, $\epsilon$-N-methyllysine, $\epsilon$-N,N,N-trimethyllysine, aminoadipic acid, $\gamma$-carboxyglutamic acid, phosphoserine, phosphothreonine, phosphotyrosine, N-methylarginine, and N-acetyllysine. Naturally occurring amino acid residues are preferred.

In addition to naturally occurring amino acids and variants thereof, other residues that are compatible with standard solid-phase peptide synthesis protocols can be used to form the compounds described herein, as will be appreciated by those of skill in the art. Representative residues include, but are not limited to, moieties such as $\beta$-amino acids and longer chain amino alkanoic acids, peptide nucleic acids, and amino benzoic acids.

Peptide segments can be varied, for example, to encourage specific cellular adhesion through integrin mediated binding (RGD tripeptide as fibronectin mimic, IKVAV as a laminin mimic, and the like) or to encourage other molecular recognition events (carboxylates to sequester metal ions, defined entities of a natural or unnatural origin to promote a chemical interaction).

As used herein, "self-assembly" is intended to mean the process by which molecules adopt a defined arrangement without guidance from an outside source.

As used herein, "supramolecular" is intended to mean relating to or denoting structures composed of several or many molecules.

As used herein, "semiconductor nanomaterials" are those materials that have electrical conductivity intermediate to that of a conductor and an insulator and have structured components with at least one dimension less than 100 nm.

As used herein, "bioelectronic nanomaterials" are those biological materials that have electronic characteristics and have structured components with at least one dimension less than 100 nm.

As used herein, a "field-effect transistor" is a transistor that uses an electric field to control the shape and hence the conductivity of a channel of one type of charge carrier in a semiconductor material.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Materials and Methods

General Considerations

THF was freshly distilled from sodium/benzophenone, or acquired from an Innovative Technologies Pure Solv solvent purification system and dried over 4 Å molecular sieves. DMF and diisopropylamine were purchased from Sigma-Aldrich and dried over 4 Å molecular sieves. Solvents were degassed by sparging with nitrogen for 30 to 90 minutes before use. Tetrakis(triphenylphosphine)palladium was obtained from Strem Chemicals. N-Methylpyrrolidone (NMP), Wang resin (preloaded with an amino acid), and Fmoc-protected amino acids were obtained from Advanced ChemTech. O-(Benzotriazol-1-yl)-N,N,N',N'-tetramethyluronium hexafluorophosphate (HBTU) was purchased from Oakwood Products Inc. Biotech grade cellulose ester dialysis tubing (MWCO 500-1000) was purchased from Spectrum Labs. All other reagents and starting materials were obtained from Sigma-Aldrich and were used as received. 2,5-bis(tributylstannyl)thiophene, 5,5'-bis-tributylstannyl-[2,2']-bithiophene, and 5'-bromo-[2,2'-bithiophene]-5-carboxylic acid were prepare using literature procedures (Hou et al., 2006; Guo et al., 2008; Kilbinger et al., 2000).

NMR Spectroscopy $^1$H-NMR spectra were obtained using a Bruker Avance 400 MHz FT-NMR spectrometer, and processed with Bruker Topspin 1.3. Peptide $^1$H NMR spectra were acquired using a 1 second presaturation pulse to suppress water.

Electrospray Ionization Mass Spectrometry (ESI-MS)

ESI samples were collected using a Thermo Finnigan LCQ Deca Ion Trap Mass Spectrometer in negative mode. Samples were prepared in a 1:1 MeOH:water solution with 0.1% ammonium hydroxide.

UV-Vis and Photoluminescence

UV-Vis spectra were obtained using a Varian Cary 50 Bio UV-Vis spectrophotometer. Photoluminescence spectra were obtained using a PTi Photon Technology International Fluorometer with an Ushio Xenon short arc lamp. Spectroscopic samples were prepared by diluting the peptide solution to the appropriate concentration (exact concentrations given in spectra captions) in Millipore water to achieve an optical density near 0.1. The pH was then adjusted by adding 10 µL of either 1M KOH (basic) or 1M HCl (acidic).

Circular Dichroism (CD)

CD spectra were obtained using a Jasco J-810 spectropolarimeter. Spectroscopic samples were prepared by diluting the peptide solution to the appropriate concentration (exact concentrations given in spectra captions) in Millipore water. The pH was then adjusted by adding 10 µL of either 1M KOH (basic) or 1M HCl (acidic).

Reverse-Phase HPLC

HPLC purification was performed on an Agilent 1100 series (semi-preparative/analytical) and a Varian PrepStar SD-1 (preparative) instruments using Luna 5 µm particle diameter C8 with TMS endcapping columns with silica solid support. An ammonium formate aqueous buffer (pH 8) and acetonitrile was used as the mobile phase.

Transmission Electron Microscopy (TEM)

Imaging was performed on a Philips EM 420 transmission electron microscope equipped with an SIS Megaview III CCD digital camera and a FEI Tecnai 12 TWIN transmission electron microscope equipped with a SIS Megaview III wide-angle camera. The samples were prepared by pipetting a drop of 1 mg/mL solution of assembled peptide in water onto 200 mesh copper grids coated with carbon and incubated for 5 minutes at 25° C. Excess solution was wicked off by touching the side of the grid to filter paper. The sample was then stained with a 2% uranyl acetate solution and excess moisture was wicked off. The grid was allowed to dry in air before imaging.

Atomic Force Microscopy (AFM)

Samples were analyzed on a Digital Instruments Nanoscope IIIa AFM, purchased from Veeco, by tapping mode. AFM tips were used as received with resonance frequencies near 320 kHz, spring constants near 42 N/m, and tip radii of 10 nm. Samples were prepared by creating a 0.1 mg/mL solution of 3 in water. The solution was subjected to concentrated HCl vapor in a closed chamber for 1 minute. 10 µL of the solution was then dropcasted atop an SiO$_2$ substrate via pipette, then pulled back up. Solution remaining on the substrate was allowed to dry before imaging.

Device Fabrication

A neutral 1 wt % solution of 4 was dropcast atop a piranha cleaned SiO$_2$ substrate and subjected to HCl vapor in a closed chamber for 3 minutes. After drying, 50 nm thick gold electrodes were thermally evaporated, at a rate of 0.4 angstroms/second, using a 200 mesh TEM grid as a shadow mask. The electrical readings were obtained using an Agilent 4155c semiconductor parameter analyzer. The mobility was calculated by fitting the transfer curve to the linear region of the field effect transistor equation:

$$I_D = \mu C_i \left(\frac{W}{L}\right) V_D (V_G - V_{th})$$

Where $I_D$ is the drain current, µ is the hole mobility, $C_i$ is the gate insulator capacitance per unit area, W and L are the width and length of the channel, respectively, $V_D$ is the drain voltage, $V_G$ is the gate voltage, and $V_{th}$ is the threshold voltage. The capacitance value for the 300 nm SiO$_2$ layer was 11.5 nF/cm$^2$ and the electrodes had a width of 60 µm and a length of 8 µm.

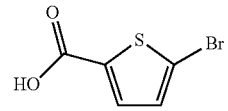

5-bromothiophene-2-carboxylic acid

THF (50 mL) was added via cannula to a flame-dried 100 mL Schlenk flask. 2,5-dibromothiophene (10 mmol, 2.42 g) was added via syringe. Reaction vessel was cooled to −78° C. and n-butyllithium (1.61M solution in hexanes, 11 mmol, 6.8 mL) was added dropwise over 5 minutes. The solution was allowed to stir at −78° C. for 1 hr. Dry ice (approx. 50 g) was added to the reaction mixture, and was allowed to stir and return to room temperature for 18 hrs. under nitrogen. The light gray suspension was filtered and the white solid was stirred in 2M HCl for 1 hr. The suspension was filtered to yield a white solid (5.7 mmol, 1.2 g, 57%). $^1$H NMR (400 MHz, CDCl$_3$) δ: 11.45 (br s, 1H), 7.64 (d, 1H, J=4.0 Hz), 7.11 (dd, 1H, J=4.0 Hz).

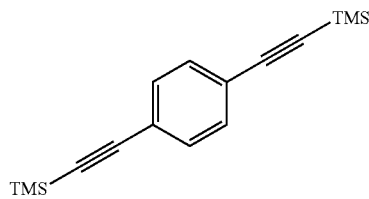 [SMILES: C[Si](C)(C)C#Cc1ccc(C#C[Si](C)(C)C)cc1]

1,4-bis((trimethylsilyl)ethynyl)benzene 40 mL THF was transferred to a flame-dried Schlenk flask. 1,4-dibromobenzene (2.5 mmol, 0.060 g), Pd(PPh$_3$)$_4$ (0.1 mmol 0.12 g), and CuI (0.2 mmol, 0.004 g) were added. Trimethylsilylacetylene (6 mmol, 0.87 mL) and 10 mL DIPA was added via syringe. The mixture was heated to 45° C. for 24 hrs. under nitrogen. The resulting suspension was filtered and filtrate was concentrated under reduced pressure. The residual solid was dissolved in dichloromethane and washed with an aqueous ammonium chloride solution. The organic layer was concentrated and crude product was subjected to column chromatography (silica, hexanes) to afford a white solid (2.3 mmol, 0.61 g, 90% yield). $^1$H NMR (400 MHz, CDCl$_3$) δ: 7.37 (s, 4H), 0.22 (s, 18H).

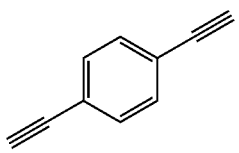

1,4-diethynylbenzene

Methanol was added to a 100 mL round-bottomed flask. 1,4-bis((trimethylsilyl)ethynyl)benzene (0.63 mmol, 0.17 g) and K$_2$CO$_3$ (3.2 mmol, 0.44 g) were added. The mixture was allowed to stir at room temperature for 1 hr. under nitrogen. Methanol was removed under reduced pressure. Residual white solid was dissolved in water and washed twice with ether. The organic layer was collected and solvent removed under reduced pressure to yield a white solid (0.47 mmol, 0.059 g, 15%), which was used immediately without further purification. $^1$H NMR (400 MHz, CDCl$_3$) δ: 7.42 (s, 2H), 3.15 (s, 1H).

General Solid Phase Peptide Synthesis (SPPS) Procedure

Peptides were synthesized via standard SPPS using Fmoc-protected amino acids, starting from Wang resin preloaded with the first amino acid, within a peptide chamber (Wang-Asp=0.8 mmol/g, Wang-Val=0.67 mmol/g). Fmoc deprotection was completed through treating the resin with a 20% piperidine solution in DMF twice for 10 minutes. The resin was washed 3× each with NMP, methanol, and DCM. Amino acid couplings were performed by external activation of 3 eq. of the Fmoc-protected amino acid, relative to resin loading, with 2.9 eq. of HBTU and 10 eq. of diisopropylethylamine, which was then added to the peptide chamber and agitated for 45-90 minutes. After coupling, the resin was again washed 3× each with NMP, methanol, and DCM. All couplings were monitored using a Kaiser test on a few dry resin beads. The procedure was repeated until the desired oligopeptide sequence was obtained.

General N-Acylation Procedure of Peptides

Following completion and deprotection of the oligopeptide, the resin was treated with an aryl halide carboxylic acid (3 eq.) that was activated by HBTU (2.9 eq.) and diisopropylethylamine (10 eq.) for 2-3 hours, leading to an N-acylated peptide capped with the desired aryl halide. The coupling was monitored using a Kaiser test on a few dry resin beads. After completion, the resin was subjected to a standard wash cycle: 3×NMP, 3×DMF, 2× isopropanol, 2× water, 2× (2×THF, 2× isopropanol), 2× acetonitrile, 2× diethyl ether, 2× hexanes.

General on-Resin Stille Coupling Procedure

The solid supported peptide capped with an aryl halide was made following the general SPPS and N-acylation procedures. The resin (1 eq.) was transferred to a Schlenk flask equipped with a reflux condenser. The resin was dried under vacuum. Pd(PPh$_3$)$_4$ (4 mol %, relative to resin loading) was added to the reaction vessel. An approximately 15 mM solution of the bis-stannylated aryl reagent (0.5 eq) was prepared in DMF. The solution was added to the reaction flask via syringe. The mixture was heated to 80° C. for 16-21 hrs. and was agitated constantly by bubbling nitrogen through the solution. The mixture was allowed to cool to room temperature. The peptide was subjected to the general cleavage and work-up procedure to yield the crude product, then further purified by HPLC.

General on-Resin Suzuki Coupling Procedure

The solid supported peptide capped with an aryl halide was made following the general SPPS and N-acylation procedures. The resin (1 eq.) was transferred to a Schlenk flask equipped with a reflux condenser. The resin was dried under vacuum. Pd(PPh$_3$)$_4$ (4 mol % relative to resin loading) and benzene-1,4-diboronic acid (0.55 eq.) was added to the reaction vessel. K$_2$CO$_3$ (8 eq.) was dissolved in 0.5 mL of water and was added to the reaction flask along with 5-10 mL DMF via syringe. The mixture was heated to 80° C. for 20-27 hrs. and was agitated constantly by bubbling nitrogen through the solution. The mixture was allowed to cool to room temperature. The resin was washed with water and then subjected to the general cleavage and work-up procedure to yield the crude product, then further purified by HPLC.

General Cleavage, Work-Up Procedure of Peptides

Following solid-phase cross-coupling, the resin was returned to the peptide chamber and again subjected to a standard wash cycle: 3×NMP, 3×DMF, 2× isopropanol, 2× water, 2× (2×THF, 2× isopropanol), 2× acetonitrile, 2× diethyl ether, 2× hexanes. The resin was treated with 9.5 mL of trifluoroacetic acid, 250 μL water, and 250 μL of triisopropylsilane for 3 hrs. The peptide solution was filtered from the resin beads, washed 3× with DCM, and was concentrated by evaporation under reduced pressure. The crude peptide was then precipitated from solution with 90 mL of diethyl ether and isolated through centrifugation. The resulting pellet was triturated with diethyl ether to yield crude product, which was dissolved in approximately 2 mL of water and 30 μL ammonium hydroxide and lyophilized. The crude peptide was then dissolved in 5-10 mL of water. The solution was placed inside dialysis tubing of the appropriate length. The tubing was stirred in 1 L of water for 2 hours. After 2 hours, the water was exchanged and the tubing was allowed to stir for another 2 hours. The water was exchanged once again, and the tubing stirred overnight (approx. 15 hours). The tubing was then removed from water, and the peptide solution transferred to a separate container and lyophilized.

DFAG-OT3-GAFD Peptide (1)

Solid supported Wang-DFAG-NH$_2$ peptide N-acylated with 5-bromothiophene-2-carboxylic acid was prepared (0.1 mmol). The resin was subjected to the standard Stille coupling procedure in the presence of 2,5-bis(tributylstannyl)thiophene (0.050 mmol, 0.033 g) and Pd(PPh$_3$)$_4$ (0.004 mmol, 0.005 g) for 21 hours. Following general cleavage and work-up, the peptide was obtained as a yellow powder (0.016 mmol, 0.018 g, 32% yield). Following HPLC purification, 0.006 mmol, 0.007 g, 12% yield. $^1$H NMR (400 MHz, D$_2$O) δ: 7.51 (d, 2H, J=3.9 Hz), 7.31-7.26 (m, 8H), 7.21-7.18 (m, 2H), 7.16 (br s, 2H), 7.09 (br s, 2H), 4.70 (dd, 2H, J=7.3, 4.9 Hz), 4.41 (dd, 2H, J=8.3, 4.5 Hz), 4.3 (q, 2H, J=7.2 Hz), 4.05 (d, 2H, J=16.6 Hz), 3.93 (d, 2H, J=16.9 Hz), 3.29 (dd, 2H, J=16.0, 4.5 Hz), 3.0 (dd, 2H, J=12.0, 10.1 Hz), 2.70 (dd, 2H, J=16.0, 4.5 Hz), 2.59 (dd, 2H, J=16.0, 8.4 Hz), 1.27 (d, 6H, J=7.2 Hz). UV-Vis (H$_2$O) λ/nm (log ε): 392 (4.57). MS (ESI) m/z 1115.4 ((M-H))$^-$ (calc. 1115.3), m/z 1137.4 (M−2H+Na)$^-$ (calc. 1137.2), m/z 1159.5 (M−3H+2Na)$^-$ (calc. 1159.2), m/z 1181.5 (M−4H+3Na)$^-$ (calc. 1181.2), m/z 557.3 (M−2H)$^{-2}$ (calc. 557.1).

DFAG-OT4-GAFD Peptide (2)

Solid supported Wang-DFAG-NH$_2$ peptide N-acylated with 5-bromothiophene-2-carboxylic acid was prepared (0.3 mmol). The resin was subjected to the standard Stille coupling procedure in the presence of 5,5'-bis-tributylstannyl-[2,2']-bithiophene (0.25 mmol, 0.19 g) and Pd(PPh$_3$)$_4$ (0.012 mmol, 0.014 g) for 18 hours. Following general cleavage and work-up, the peptide was obtained as a light orange powder (0.063 mmol, 0.075 g, 42% yield). Following HPLC purification, 0.016 mmol, 0.019 g, 11% yield. $^1$H NMR (400 MHz, D$_2$O) δ: 7.45-6.20 (m, 18H), 2H, 4.65-4.61 (m, 2H), 4.40 (dd, 2H, J=7.0, 5.7 Hz), 4.31 (q, 2H, J=7.2 Hz), 3.98 (d, 2H, J=16.8 Hz), 3.88 (d, 2H, J=17.3 Hz), 3.4-3.15 (m, 2H), 3.00-2.87 (m, 2H), 2.65 (dd, 2H, J=16.7, 5.2 Hz), 2.58 (dd, 2H, J=15.5, 7.5 Hz), 1.28 (d, 6H, J=7.0 Hz). UV-Vis (H$_2$O) λ/nm (log ε): 419 (4.64). MS (ESI) m/z 1197.4 ((M-H))$^-$ (calc. 1197.2), m/z 598.6 (M-2H)$^{-2}$ (calc. 598.1), m/z 399.0 (M-3H)$^{-3}$ (calc. 398.4), m/z 1219.4 (M-2H+Na)$^{-1}$ (calc. 1219.2).

DADGG-OT5-GGDAD Peptide (3)

Solid supported Wang-DADGG-NH$_2$ peptide N-acylated with 5'-bromo-[2,2'-bithiophene]-5-carboxylic acid was prepared (0.3 mmol). The resin was subjected to the standard Stille coupling procedure in the presence of 2,5-bis(tributylstannyl)thiophene (0.15 mmol, 0.10 g) and Pd(PPh$_3$)$_4$ (0.012 mmol, 0.014 g) for 18 hours. Following general cleavage and work-up, the peptide was obtained as an orange powder (0.037 mmol, 0.049 g, 25% yield). Following HPLC purification, 0.015 mmol, 0.020 g, 10% yield. $^1$H NMR (400 MHz, D$_2$O) δ: 7.52 (d, 2H, J=3.4), 7.23-7.15 (m, 2H), 7.14-7.09 (m, 2H), 7.09-7.02 (m, 4H), 4.64 (dd, 2H, J=8.9, 4.6 Hz), 4.39-4.33 (m, 4H), 4.14-3.96 (m, 8H), 2.74 (dd, 2H, J=16.1, 4.6), 2.66 (dd, 2H, J=15.8, 4.3), 2.62 (dd, 2H, J=14.6, 9), 2.54 (dd, 2H, J=15.7, 9.2), 1.36 (d, 6H, J=7.2). UV-Vis (H$_2$O) λ/nm (log ε): 433 (4.65). MS (ESI) m/z 1329.4 ((M-H))$^-$ (calc. 1329.2), m/z 664.7 (M-2H)$^{-2}$ (calc. 664.1), m/z 442.9 (M-3H)$^{-3}$ (calc. 442.4), m/z 332.1 (M-4H)$^{-4}$ (calc. 331.5), m/z 1373.4 (M-3H+2Na)$^{-1}$ (calc. 1374.3).

DADDG-OT6-GDDAD Peptide (4)

Solid supported Wang-DADDG-NH$_2$ peptide N-acylated with 5'-bromo-[2,2'-bithiophene]-5-carboxylic acid was prepared (0.3 mmol). The resin was subjected to the standard Stille coupling procedure in the presence of 5,5'-bis-tributylstannyl-[2,2']-bithiophene (0.150 mmol, 0.112 g) and Pd(PPh$_3$)$_4$ (0.012 mmol, 0.014 g) for 16 hours. Following general cleavage and work-up, the peptide was obtained as an orange powder (0.048 mmol, 0.073 g, 32% yield). Following HPLC purification, 0.004 mmol, 0.007 g, 3% yield. $^1$H NMR (400 MHz, D$_2$O) δ: 7.47 (s, 2H), 7.20-6.80 (m, 4H), 6.80-6.46 (m, 2H), 4.65 (dd, 2H, J=5.5, 2.0 Hz), 4.35 (dd, 2H, J=8.7, 4.6 Hz), 4.32-4.22 (m, 2H), 4.20-4.00 (m, 2H), 2.85-2.69 (m, 4H), 2.69-2.58 (m, 6H), 2.53 (dd, 2H, J=15.0, 8.7 Hz), 1.34 (br s, 6H). UV-Vis (H$_2$O) λ/nm (log ε): 447 (4.76). MS (ESI) m/z 763.3 (M-2H)$^{-2}$ (calc. 763.1), m/z 381.2 (M-4H)$^{-4}$ (calc. 381.0), m/z 386.7 (M-5H+Na)$^{-4}$ (calc. 386.5), m/z 515.9 (M-4H+Na)$^{-3}$ (calc. 515.7), m/z 774.3 (M-3H+Na)$^{-2}$ (calc. 774.1).

VEVAG-PTP-GAVEV Peptide (5)

Solid supported Wang-VEVAG-NH$_2$ peptide N-acylated with 4-iodobenzoic acid was prepared (0.1 mmol). The resin was subjected to the standard Stille coupling procedure in the presence of 2,5-bis(tributylstannyl)thiophene (0.050 mmol, 0.037 g) and Pd(PPh$_3$)$_4$ (0.004 mmol, 0.005 g) for 21 hours. Following general cleavage and work-up, the peptide was obtained as a pale yellow powder (0.028 mmol, 0.034 g, 54% yield). Following HPLC purification, 0.005 mmol, 0.006 g, 10% yield. $^1$H NMR (400 MHz, D$_2$O) δ: 7.74 (d, 4H, J=8.4 Hz), 7.65 (d, 4H, J=8.4 Hz), 7.44 (s, 2H), 4.43 (q, 2H, J=7.3 Hz), 4.35 (dd, 2H, J=9.2, 5.4 Hz), 4.15 (d, 2H, J=7.6 Hz), 4.13-4.00 (m, 6H), 2.34-2.16 (m, 4H), 2.14-1.99 (m, 6H), 1.98-1.84 (m, 2H), 1.40 (d, 6H, J=7.2 Hz), 0.94 (d, 12H, J=6.7 Hz), 0.90 (d, 6H, J=7.3 Hz), 0.88 (d, 6H, J=7.1 Hz). UV-Vis (H$_2$O) λ/nm (log ε): 352 (4.54). MS (ESI) m/z 1233.6 ((M-H))$^-$ (calc. 1233.5), m/z 616.5 (M-2H)$^{-2}$ (calc. 616.3), m/z 627.5 (M-3H+Na)$^{-2}$ (calc. 627.2), m/z 638.6 (M-4H+2Na)$^{-2}$ (calc. 638.2), m/z 1277.6 (M-3H+2Na)$^-$ (calc. 1277.5), m/z 1299.6 (M-4H+3Na)$^{-1}$ (calc. 1299.5).

VEVAG-OP3-GAVEV Peptide (6)

Solid supported Wang-VEVAG-NH$_2$ peptide N-acylated with 4-iodobenzoic acid was prepared (0.5 mmol). The resin was subjected to the standard Suzuki coupling procedure for 20 hours. Following general cleavage and work-up, the peptide was obtained as a white powder (0.53 mmol, 0.65 g, 211% yield). Following HPLC purification, 0.014 mmol, 0.017 g, 5% yield. $^1$H NMR (400 MHz, D$_2$O) δ: 7.94 (d, 4H, J=8.5 Hz), 7.90-7.85 (m, 8H), 4.45 (q, 2H, J=7.1 Hz), 4.36 (dd, 2H, J=9.3, 5.3 Hz), 4.22-4.14 (m, 4H), 4.11 (d, 2H, J=8.4 Hz), 4.05 (d, 2H, J=5.88 Hz), 2.34-2.16 (m, 4H), 2.16-2.00 (m, 6H), 1.98-1.86 (m, 2H), 1.41 (d, 6H, J=7.2 Hz), 0.95 (d, 6H, J=6.8 Hz), 0.95 (d, 6H, J=6.7 Hz), 0.90 (d, 6H, J=7.1 Hz), 0.88 (d, 6H, J=7.0 Hz). UV-Vis (H$_2$O) λ/nm (log E): 301 (4.74). MS (ESI) m/z 1227.9 ((M-H))$^-$ (calc. 1227.6), m/z 613.8 (M-2H)$^{-2}$ (calc. 613.3), m/z 624.8 (M-3H+Na)$^{-2}$ (calc. 624.3), m/z 408.8 (M-3H)$^{-3}$ (calc. 408.5), m/z 306.6 (M-4H)$^{-4}$ (calc. 306.1), m/z 1249.8 (M-2H+Na)$^{-1}$ (calc. 1249.5), m/z 1293.8 (M-4H+3Na)$^{-1}$ (calc. 1293.5).

VEVAG-TPT-GAVEV Peptide (7)

Solid supported Wang-VEVAG-NH$_2$ peptide N-acylated with 5-bromothiophene-2-carboxylic acid was prepared (0.1 mmol). The resin was subjected to the standard Suzuki coupling procedure for 27 hours. Following general cleavage and work-up, the peptide was obtained as a white powder (0.016 mmol, 0.020 g, 32% yield). Following HPLC purification, 0.001 mmol, 0.002 g, 2.5% yield. $^1$H NMR (400 MHz, D$_2$O) δ: 7.77 (s, 4H), 7.71 (d, 2H, J=4.0 Hz), 7.50 (d, 2H, J=4.0 Hz), 4.43 (q, 2H, J=7.2 Hz), 4.34 (dd, 2H, J=9.3, 5.3 Hz), 4.16 (d, 2H, J=7.6 Hz), 4.14 (d, 2H, J=16.6 Hz), 4.07 (d, 2H, J=16.8 Hz), 4.05 (d, 2H, J=5.8 Hz), 2.33-2.16 (m, 4H), 2.14-1.99 (m, 6H), 1.97-1.86 (m, 2H), 1.41 (d, 6H, J=7.2 Hz), 0.95 (d, 6H, J=6.8 Hz), 0.94 (d, 6H, J=6.8 Hz), 0.90 (d, 6H, J=6.8 Hz), 0.88 (d, 6H, J=6.8 Hz). UV-Vis (H$_2$O) λ/nm (log ε): 356 (4.51). MS (ESI) m/z 1239.6 ((M-H))$^-$ (calc. 1239.5), m/z 1283.7 (M-3H+2Na)$^-$ (calc. 1283.4), m/z 1305.7 (M-4H+3Na)$^-$ (calc. 1305.4), m/z 619.8 (M-2H)$^{-2}$ (calc. 619.2).

DFAG-OPE3-GAFD Peptide (8)

Solid supported Wang-DFAG-NH$_2$ peptide N-acylated with 4-iodobenzoic acid was prepared following the general SPPS and N-acylation procedures. The resin (0.3 mmol) was transferred to a Schlenk flask and dried under vacuum. Pd(PPh$_3$)$_4$ (0.015 mmol, 0.017 g) CuI (0.03 mmol, 0.006 g) and 1,4-diethynylbenzene (0.17 mmol, 0.021 g) were added to the reaction vessel. 3 mL of diisopropyl amine and 7 mL of DMF were added to the flask via syringe. The mixture was agitated constantly by bubbling nitrogen through the solution at room temperature for 18 hrs. The resin was washed with water and then subjected to the standard cleavage (triisopropylsilane was omitted from the cleavage cocktail) and work-up procedure. The peptide was obtained as a white powder (0.054 mmol, 0.062 g, 36% yield). Following HPLC purification, 0.002 mmol, 0.018 g, 11% yield. $^1$H NMR (400 MHz, D$_2$O) δ: 7.87-7.50 (m, 12H,), 7.50-7.10 (m, 10H), 4.39 (dd, 2H, J=8.8, 4.2 Hz), 4.30-4.20 (m, 2H), 4.11 (d, 2H, J=17.1 Hz), 4.00 (d, 2H, J=15.0 Hz), 3.37-3.23 (m, 2H), 2.94 (dd, 2H, J=13.2, 10.8 Hz), 2.65 (dd, 2H, J=15.8, 3.9 Hz), 2.54 (dd, 2H, J=16.0, 9.2 Hz), 1.23 (d, 6H, J=5.8 Hz). UV-Vis (H$_2$O)/nm (log E): 332 (4.80). (ESI) m/z 572.5 (M-2H)$^{-2}$ (calc. 572.1), m/z 1167.4 (M-2H+Na)$^-$ (calc. 1167.4), m/z 381.4 (M-3H)$^{-3}$ (calc. 381.1).

Example 2

Library of π-Conjugated Peptides

The methods of the presently disclosed subject matter have proven versatile in the straightforward synthesis of a wide range of π-conjugated peptides (Table 1).

TABLE 1

Library of π-conjugated peptides.

| Ar¹—X | Y—Ar²—Y | method | product |
|---|---|---|---|
| 5-bromothiophene-2-carboxylic acid | 5,5'-bis(tributylstannyl)-2,2'-bithiophene | Stille[c] | 1 (GAFD / DFAG) |
| 5-bromothiophene-2-carboxylic acid | 5,5'-bis(tributylstannyl)-2,2'-bithiophene | Stille[c] | 2 (GAFD / DFAG) |
| 5'-bromo-2,2'-bithiophene-5-carboxylic acid | 2,5-bis(tributylstannyl)thiophene | Stille[c] | 3 (GGDAD / DADGG) |

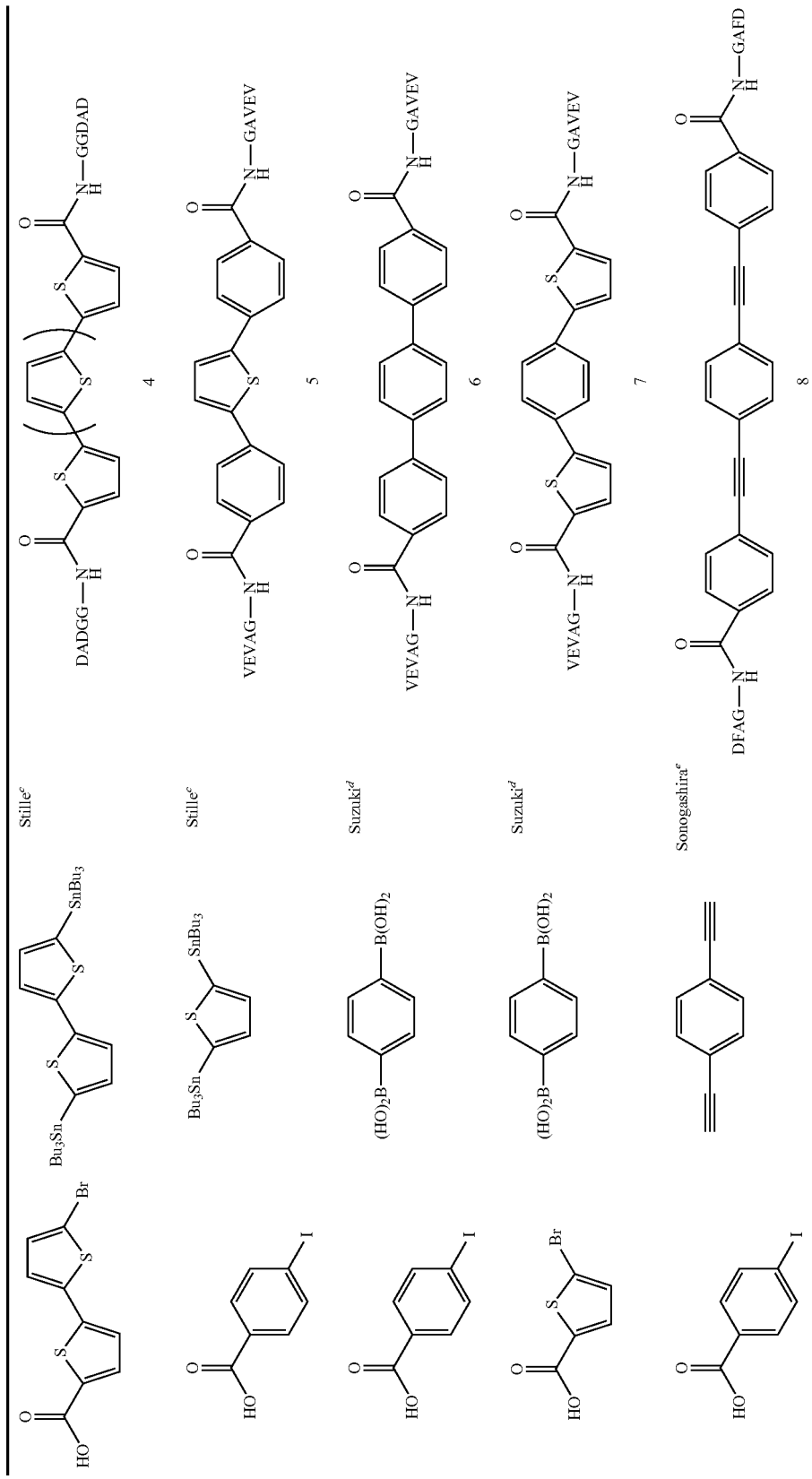

a. All equivalents were determined with respect to the amino acid loading of the peptide resin that was used (0.8-0.67 mmol/g). b. Cleavage of the peptide from the resin was performed by treating the resin to a 10:0.25:0.25 cocktail of TFA:TIPS:$H_2O$ for 3 hours. c. Stille reaction conditions utilized 0.5 eq. of the distannylated arene and 4 mol % Pd($PPh_3$)$_4$ in DMF for 16-21 hours at 80° C., d. Suzuki reaction conditions utilized 0.55 eq. of benzene-1,4-diboronic acid, 4 mol % Pd($PPh_3$)$_4$, $K_2CO_3$ (8 eq), in DMF:$H_2O$ (4:1), for 20-27 hours at 80° C., e. Sonogashira reaction conditions utilized 0.55 eq. of 1,4-diethynyl benzene, 5 mol % Pd ($PPh_3$)$_4$, 10 mol % CuI, in DMF for 18 hours at RT. TIPS was omitted from cleavage cocktail.

Obtaining the same peptides using classical routes would have required the upfront preparation of requisite amino acid or diacid oligomers by way of several synthetic manipulations (cross-couplings, lithiations, chromatography, crystallizations, etc.), all on sparingly soluble products. With the methods of the presently disclosed subject matter, utilization of thiophene-based aryl components under Stille reaction conditions allowed for the formation of oligothiophene-containing peptides ranging from terthiophene (1) to sexithiophene (4), directly from simple mono- and bithiophene building blocks. Furthermore, commercially available 4-iodobenzoic acid and 1,4-benzene diboronic acid were employed under Suzuki cross-coupling conditions to obtain terphenyl peptide 6. The method also provides mixed aromatic systems consisting of alternating thiophene and phenyl rings using either Stille (5) or Suzuki (7) conditions. Sonogashira cross-coupling conditions, utilizing 4-iodobenzoic acid and 1,4-diethynyl benzene, provided oligophenyleneethynylene (OPE$_3$) peptide 8.

The initial synthesis attempt for 8 resulted in a partially hydrogenated alkyne product as determined by NMR, potentially due to a small amount of remaining palladium catalyst and the presence of triisopropylsilane during cleavage (Luo et al., 2010). To remedy this, the silane was eliminated from the cleavage cocktail, and the partial hydrogenation side-reaction was no longer seen. The fairly sensitive OPE$_3$ chromophore remained intact, despite the harsh acidic cleavage conditions, thereby suggesting that other comparably sensitive i-electron units will tolerate the cleavage chemistry.

The peptide sequences were chosen mainly for solubility reasons. For instance, due to the tendency of intermolecular aggregation of longer oligothiophenes, sequences containing more ionizable amino acids were selected to allow for aqueous solubility with minimal aggregation under basic pH (e.g. 3,4). Under these conditions, the carboxylic acid groups are deprotonated, thus exploiting charge repulsion to prevent intermolecular association. The UV-vis absorption spectra of 1-4 in water at pH 8 (FIG. 1) showed an increasingly redshifted $\lambda_{max}$ from 392 nm (1) to 447 nm (4), owing to the increasing conjugation length of the embedded oligothiophene subunit with minimal complications from scattering.

Example 3

Self-Assembly of Peptides Embedded with Complex Organic Electronic Subunits

Intermolecular self-assembly is expected to occur via favorable hydrogen bonding (FIGS. 2a and 2b) to create networks of π-stacking among the embedded chromophores. The exciton coupling among the electronic transition dipoles of these π-electron units in an H-like fashion has been established (Schillinger et al., 2009; Stone et al., 2009; Vadehra et al., 2010). However, without wishing to be bound to any one particular theory, it is conceivable that longer π-conjugated oligomers here might have less enthalpically favored cofacial π-stacking. More significant quadrupole repulsions between longer conjugated oligomers could potentially drive assembly into a slip-stack type of orientation with less cofacial overlap, competing with the formation of hydrogen bonding networks among the peptide scaffolds. Absorption and photoluminescence data were acquired for all peptides in both their unassembled (pH 8) and assembled (pH 6) states in order to assess these electronic interactions.

Upon self-assembly, all peptides displayed a blue shift in the absorption and quenching of the photoluminescence, indicative of H-like aggregation of the chromophore subunits (Kasha et al., 1965). The data shown for 4 (FIG. 2c) under basic (dashed lines) and acidic (solid lines) conditions is representative.

Figure 2:
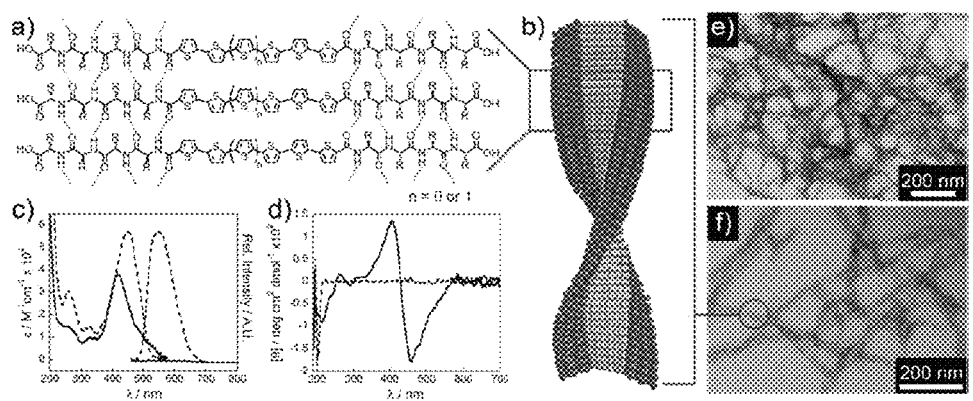

Upon self-assembly, 4 displays a 32 nm blue shift in the $\lambda_{max}$ and almost complete quenching of photoluminescence. Circular dichroism spectra were also obtained for each peptide, and the spectra from 4 are shown in FIG. 2d. Similar to typical peptidic molecules of this sort, 4 showed no meaningful absorption when in basic solution. Acidic, self-assembled samples of the peptides showed characteristic bisignate Cotton effects, where the ellipticity is zero at the $\lambda_{max}$ (415 nm) of the assembled peptide. Without wishing to be bound to any one particular theory, this suggests that the transition dipoles of the chromophore subunits embedded in the peptides interact via exciton coupling within the chiral environment imposed by tertiary structure when the molecules are assembled, in a manner that remains consistent with H-like aggregation despite the greater quadrupole influence.

TEM imaging was used to characterize nanostructure morphologies (FIGS. 2e and 2f). 1-D nanostructure assemblies of 3 on the order of microns in length were observed, comparable to those seen from peptides with less complex π-electron units (Diegelmann et al., 2008; Schillinger et al., 2009; Stone et al., 2009; Shaytan et al., 2011; Wall et al., 2011; Mba et al., 2011). TEM images of 4 also revealed nanostructures, although smaller in comparison (on the order of hundreds of nanometers in length, FIG. 3). Without wishing to be bound to any one particular theory, the shorter length may be due to the highly charged peptide sequence chosen to maintain solubility, or due to enhanced quadrupole repulsions between conjugated oligomeric subunits.

AFM also was used to investigate the nanostructures of 3 (as a representative example), which supported TEM data. Height profiles of solitary structures in AFM micrographs were found to be between 2-5 nm in height. Micrographs and height profiles are shown in FIGS. 4-7.

Example 4

Transport of Positive Charges Through the Sexithiophene Nanostructures

To demonstrate the electrical properties available through the inclusion of longer oligothiophene oligomers within peptide backbones, the nanostructures of sexithiophene 4 were incorporated as the active layer of a field effect transistor. A solution of 4 was dropcast atop an $SiO_2$ substrate and assembled by treatment with HCl vapor. After drying, gold electrodes were evaporated. FIG. 8a depicts the current-voltage output of the transistor at applied gate voltages of 20V to −80V. The hole mobility of the nanostructures of 4 was found to be 3.8×$10^{-5}$ $cm^2$ $V^{-1}$ $s^{-1}$ by fitting the transfer curve (FIG. 8b) data to the linear equation for transistor current. The mobility shows that positive charges can be transported throughout the networks of self-assembled nanostructures. Due to the crystallinity of the dropcast film, evident under a light microscope (FIG. 9), and the significant amount of insulating side chains, which can increase resistance in the sample, the magnitude of the mobility should not be expected to scale with those of high quality, crystalline organic semiconductors.

Example 5

Summary

The presently disclosed subject matter provides a solid-phase palladium-catalyzed cross-coupling dimerization method in conjunction with standard SPPS. The method grants access to π-conjugated peptides by utilizing soluble, small components, most of which are commercially available, to synthesize π-electron oligomer units on the solid phase. The procedure has allowed for the formation of a diverse array of complex optoelectronic peptide architectures, including the longest aqueous self-assembling oligothiophene-containing system to date.

The notorious insolubilities of long π-conjugated oligomeric subunits, such as quinque- and sexithiophene, which has previously complicated synthetic work, is no longer an issue for this peptide synthesis, and once incorporated in a peptide backbone, these extended systems are water soluble and easily manipulated. Each peptide, including the novel sexithiophene 4, displayed spectral features indicative of H-like aggregation when self-assembly was triggered. Nanostructures of the longer oligothiophene-containing systems (2, 3, 4) were visualized under TEM, although 4 displayed a lower aspect ratio. Furthermore, a dropcast film of assembled 4, incorporated into a field effect transistor, displayed a hole mobility of $3.8 \times 10^{-5}$ $CM^2$ $V^{-1}$ $s^{-1}$. The combination of tunable electronic structures, substantial conductance, and ability to self-assemble under aqueous conditions highlights the prospects for these peptide materials to be viable in a wide variety of uses.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Ashkenasy, N.; Home, W. S.; Ghadiri, M. R. *Small.* 2006, 2, 99-102;
Blackwell, H. E.; Clemons, P. A.; Schreiber, S. L. *Org. Lett.* 2001, 3, 1185-1188;
Bräse, S.; Kirchhoff, J. H.; Köbberling, *J. Tetrahedron.* 2003, 59, 885-939;
Chen, L.; Revel, S.; Morris, K.; Adams, D. J. *Chem. Commun.* 2010, 46, 4267-4269;
Conde-Frieboes, K.; Andersen, S.; Breinholt, *J. Tet. Lett.* 2000, 41, 9153-9156;
Deshpande, M. S. *Tet. Lett.* 1994, 35, 5613-5614;
Diegelmann, S. R.; Gorham, J. M.; Tovar, J. D. *J. Am. Chem. Soc.* 2008, 130, 13840-13841;
Doan, N.-D.; Bourgault, S.; Létourneau, M.; Fournier, A. J. *Comb. Chem.* 2008, 10, 44-51;
Guo, X.; Watson, M. D. *Org Lett.* 2008, 10 (23), 5333-5336.
Hou, J.; Tan, Z.; Yan, Y.; He, Y., Yang, C.; Li, Y. *J. Am. Chem. Soc.* 2006, 128 (14), 4911-4916.
Kas, o. Y.; Charati, M. B.; Rothberg, L. J.; Galvin, M. E.; Kiick, K. L. *J. Mater. Chem.* 2008, 18, 3847-3854;
Kasha, M.; Rawls, H. R.; Ashraf El-Bayoumi, M. *Pure Appl. Chem.* 1965, 11, 371;
Kilbinger, A. F. M.; Schenning, A. P. H. J.; Goldoni, F.; Feast, W. J.; Meijer, E. W. *J. Am. Chem. Soc.* 2000, 122 (8), 1820-1821.
Krieg, E.; Shirman, E.; Weissman, H.; Shimani, E.; Wolf, S. G.; Pinkas, I.; Rybtchinski, B. *J. Am. Chem. Soc.* 2009, 131, 14365-14373;
Kumar, R. J.; MacDonald, J. M.; Singh, T. M.; Waddington, L. J.; Holmes, A. B. *J. Am. Chem. Soc.* 2011, 133, 8564-8573;
Le Quement, S. T.; Ishoey, M.; Petersen, M. T.; Thastrup, J.; Hagel, G.; Nielsen, T. E. *ACS Comb Sci.* 2011, 13, 667-675;
Liao, Y.; Fathi, R.; Yang, Z. *J. Comb. Chem.* 2003, 5, 79-81;
Liao, Y.; Fathi, R.; Yang, Z. *Org. Lett.* 2003, 5, 909-912;
Luo, F.; Pan, C.; Wang, W.; Ye, Z.; Cheng, *J. Tetrahedron.* 2010, 66, 1399;
Malenfant, P. R. L.; Fréchet, J. M. J. *Chem Commun.* 1998, 2657-2658;
Mba, M.; Moretto, A.; Armelao, L.; Crisma, M.; Toniolo, C.; Maggini, M. *Chem. Eur. J.* 2011, 17, 2044-2047;
Olenyuk, B.; Jitianu, C.; Dervan, P. B. *J. Am. Chem. Soc.* 2003, 125, 4741-4751;
Schillinger, E.-K.; Mena-Osteritz, E.; Hentschel, J.; Börner, H. G.; Bäuerle, P. *Adv. Mater.* 2009, 21, 1562-1567;
Shao, H.; Parquette, J. R. *Chem Commun.* 2010, 46, 4285-4287;
Shaytan, A. K.; Schillinger, E.-K.; Khalatur, P. G.; Mena-Osteritz, E.; Hentschel, J.; Börner, H. G.; Bäuerle, P.; Khokhlov, A. R. *ACS Nano.* 2011, 5, 6894-6909;
Stone, D. A.; Hsu, L.; Stupp, S. I. *Soft Matter.* 2009, 5, 1990-1993;
Sun, Y.; He, C.; Sun, K.; Li, Y.; Dong, H.; Wang, Z.; Li, Z. *Langmuir.* 2011, 27, 11364-11371.
Testero, S. A.; Mata, E. G. *J. Comb. Chem.* 2008, 10, 487-497;
Tian, L.; Szilluweit, R.; Marty, R.; Bertschi, L.; Zerson, M.; Spitzner, E.-C.; Magerle, R.; Frauenrath, H. *Chem. Sci.* 2012, 3, 1512-1521;
Vadehra, G. S.; Wall, B. D.; Diegelmann, S. R.; Tovar, J. D. *Chem. Commun.* 2010, 46, 3947-3949;
Wall, B. D.; Diegelmann, S. R.; Zhang, S.; Dawidczyk, T. J.; Wilson, W. L.; Katz, H. E.; Mao, H.-Q.; Tovar, J. D. *Adv. Mater.* 2011, 23, 5009-5014;

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for preparing one or more peptide-[(Ar$^1$—Ar$^2$—Ar$^1$)]-peptide structures, the method comprising:
    a) providing one or more peptides immobilized on a solid support, wherein the one or more peptides have a deprotected or free amine group;
    b) contacting the one or more immobilized peptides with a portion of a π-conjugated subunit comprising a first arene (Ar$^1$) and differentially substituted with a halide and a carboxylic acid group to promote N-acylation of the amine termini of the one or more peptides;
c) contacting the one or more immobilized peptides of step (b) with a second arene (Ar²) disubstituted with mutually reactive functionality for transmetallation in the presence of a palladium catalyst to promote site-site cross coupling dimerization between the disubstituted second arene and the two N-acylated amine termini of the one or more peptides formed in step (b); and
d) cleaving the product formed in step (c) to form one or more peptide-[(Ar¹—Ar²—Ar¹)]-peptide structures.

2. The method of claim 1, wherein the first arene and the second arene can be the same or different and are each independently selected from the group consisting of thiophenyl, bithiophenyl, phenyl, and 1,4-diethynylphenyl.

3. The method of claim 1, wherein the halide is selected from the group consisting of bromine and iodine.

4. The method of claim 1, wherein the palladium catalyst is Pd(PPh$_3$)$_4$.

5. The method of claim 1, wherein the one or more peptide-[(Ar¹—Ar²—Ar¹)]-peptide structures are water soluble.

6. The method of claim 1, wherein the one or more peptide-[(Ar¹—Ar²—Ar¹)]-peptide structures are selected from the group consisting of:

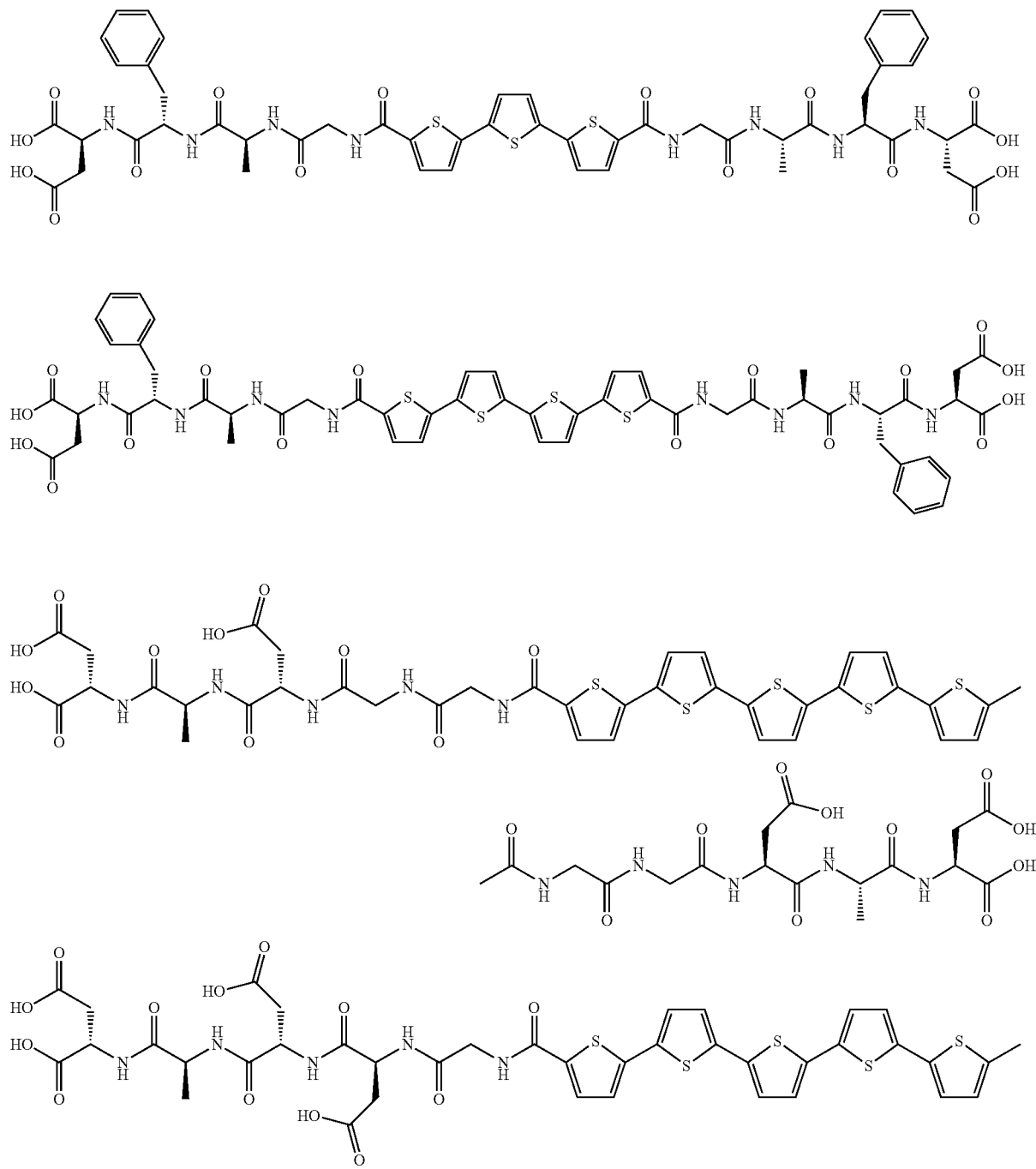

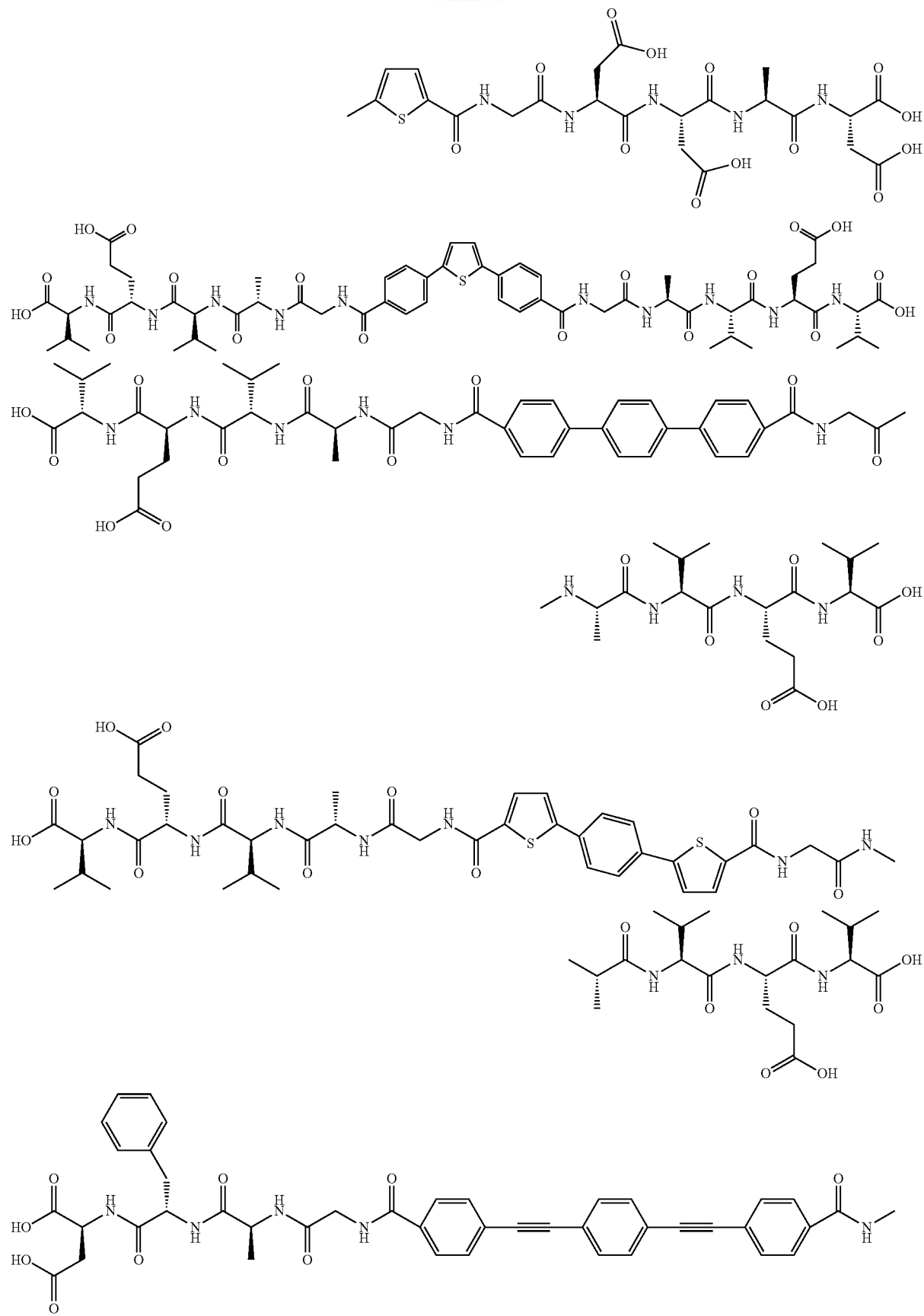

-continued
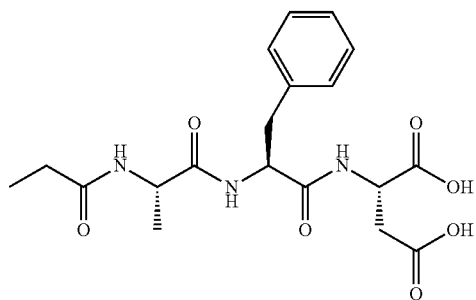
7. The method of claim 1, comprising forming one or more peptide-[(Ar$^1$—Ar$^2$—Ar$^1$)]-peptide structures comprising up to six π-conjugated units.
* * * * *